United States Patent
Ye et al.

(10) Patent No.: US 9,534,225 B2
(45) Date of Patent: Jan. 3, 2017

(54) CODON OPTIMIZED NUCLEIC ACID ENCODING A RETINITIS PIGMENTOSA GTPASE REGULATOR (RPGR)

(71) Applicants: Guo-Jie Ye, Gainesville, FL (US); Jilin Liu, Gainesville, FL (US)

(72) Inventors: Guo-Jie Ye, Gainesville, FL (US); Jilin Liu, Gainesville, FL (US)

(73) Assignee: Applied Genetic Technologies Corporation, Alachua, FL (US)

( * ) Notice: Subject to any disclaimer, the term of this patent is extended or adjusted under 35 U.S.C. 154(b) by 0 days.

(21) Appl. No.: 14/687,227

(22) Filed: Apr. 15, 2015

(65) Prior Publication Data

US 2015/0353938 A1    Dec. 10, 2015

Related U.S. Application Data

(60) Provisional application No. 61/979,633, filed on Apr. 15, 2014.

(51) Int. Cl.
| | |
|---|---|
| *C12N 9/00* | (2006.01) |
| *C12N 15/68* | (2006.01) |
| *C07K 14/47* | (2006.01) |
| *C12N 15/00* | (2006.01) |
| *C12N 15/64* | (2006.01) |

(52) U.S. Cl.
CPC .......... *C12N 15/68* (2013.01); *C07K 14/4702* (2013.01); *C12N 9/00* (2013.01); *C12N 15/00* (2013.01); *C12N 15/64* (2013.01)

(58) Field of Classification Search
CPC ....... C07K 12/4702; C12N 9/00; C12N 15/68; C12N 15/8645
USPC ............. 424/93.2, 93.6; 435/320.1; 536/23.5
See application file for complete search history.

(56) References Cited

U.S. PATENT DOCUMENTS

| | | |
|---|---|---|
| 2007/0077228 A1 | 4/2007 | Acland et al. |
| 2009/0011040 A1 | 1/2009 | Naash et al. |
| 2014/0010861 A1 | 1/2014 | Bancel et al. |

FOREIGN PATENT DOCUMENTS

| | | |
|---|---|---|
| WO | 2009/097129 A1 | 8/2009 |
| WO | 2014/011210 A1 | 1/2014 |
| WO | WO 2014/011210 * | 1/2014 |

* cited by examiner

*Primary Examiner* — Kevin Hill
(74) *Attorney, Agent, or Firm* — McCarter & English, LLP; Cristin H. Cowles

(57) ABSTRACT

This invention relates generally to a codon optimized nucleic acid encoding a retinitis pigmentosa GTPase regulator (RPGR) protein. The nucleic acid has enhanced stability during plasmid production relative to a wildtype cDNA encoding the RPGR protein. The invention also relates to expression cassettes, vectors, and host cells comprising the codon optimized nucleic acid. Methods for preparing a recombinant adeno-associated (rAAV) expression vector comprising the codon optimized nucleic acid sequence are also provided. The nucleic acids, expression cassettes, vectors, and host cells provided may be useful in the large scale production of rAAV expression vectors for gene therapy applications.

18 Claims, 10 Drawing Sheets

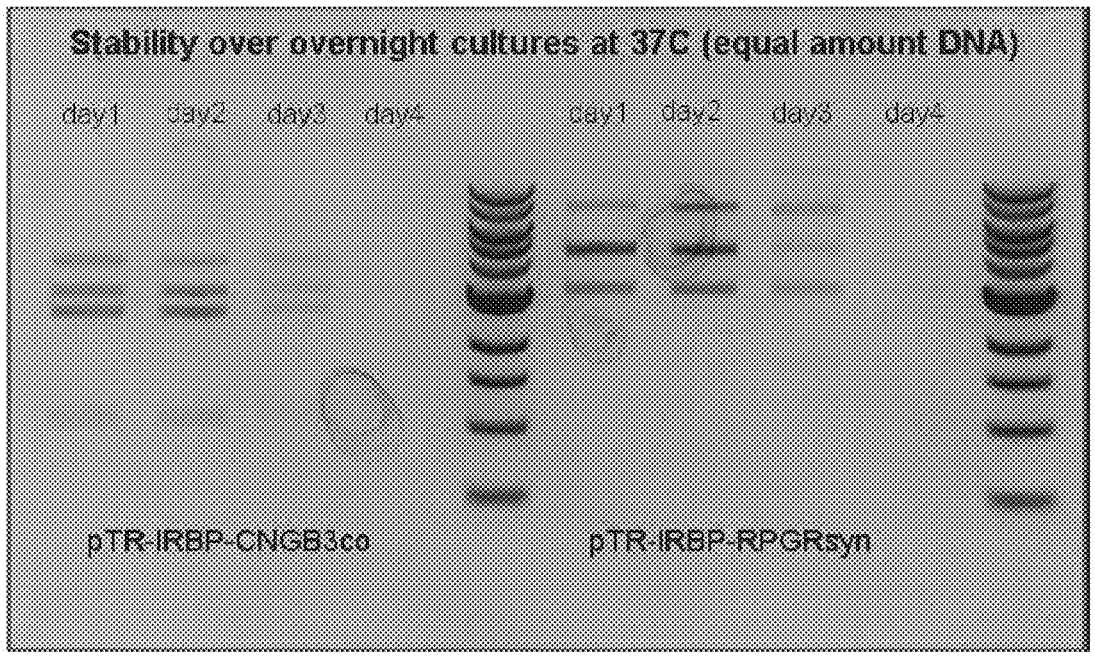

FIG. 6

```
Contig sequence      (1)   ------------------------------AGATCTGAATTCAGCACAGTGTCTG
pTR-IRBP-RPGRsyn   (3151)  GCAGAGAGGGAGTGGCCAACCTCCTAGATCTGAATTCAGCACAGTGTCTG
                                                                                  3250
                    3201
Contig sequence     (26)   GCATGTAGCAGGAACTAAAATAATGGCAGTGATTAATGTTATGATATGCA
pTR-IRBP-RPGRsyn   (3201)  GCATGTAGCAGGAACTAAAATAATGGCAGTGATTAATGTTATGATATGCA
                    3251                                                          3300
Contig sequence     (76)   GACACAACACAGCAAGATAAGATGCAATGTACCTTCTGGGTCAAACCACC
pTR-IRBP-RPGRsyn   (3251)  GACACAACACAGCAAGATAAGATGCAATGTACCTTCTGGGTCAAACCACC
                    3301                                                          3350
Contig sequence    (126)   CTGGCCACTCCTCCCCGATACCCAGGGTTGATGTGCTTGAATTAGACAGG
pTR-IRBP-RPGRsyn   (3301)  CTGGCCACTCCTCCCCGATACCCAGGGTTGATGTGCTTGAATTAGACAGG
                    3351                                                          3400
Contig sequence    (176)   ATTAAAGGCTTACTGGAGCTGGAAGCCTTGCCCCAACTCAGGAGTTTAGC
pTR-IRBP-RPGRsyn   (3351)  ATTAAAGGCTTACTGGAGCTGGAAGCCTTGCCCCAACTCAGGAGTTTAGC
                    3401                                                          3450
Contig sequence    (226)   CCCAGACCTTCTGTCCACCAGCTCTAGACTCGAGGAACTGAAAAACCAGA
pTR-IRBP-RPGRsyn   (3401)  CCCAGACCTTCTGTCCACCAGCTCTAGACTCGAGGAACTGAAAAACCAGA
                    3451                                                          3500
Contig sequence    (276)   AAGTTAACTGGTAAGTTTAGTCTTTTTGTCTTTTATTTCAGGTCCCGGAT
pTR-IRBP-RPGRsyn   (3451)  AAGTTAACTGGTAAGTTTAGTCTTTTTGTCTTTTATTTCAGGTCCCGGAT
                    3501                                                          3550
Contig sequence    (326)   CCGGTGGTGGTGCAAATCAAAGAACTGCTCCTCAGTGGATGTTGCCTTTA
pTR-IRBP-RPGRsyn   (3501)  CCGGTGGTGGTGCAAATCAAAGAACTGCTCCTCAGTGGATGTTGCCTTTA
                    3551                                                          3600
Contig sequence    (376)   CTTCTAGGCCTGTACGGAAGTGTTACTTCTGCTCTAAAAGCTGCGGAATT
pTR-IRBP-RPGRsyn   (3551)  CTTCTAGGCCTGTACGGAAGTGTTACTTCTGCTCTAAAAGCTGCGGAATT
                    3601                                                          3650
Contig sequence    (426)   GTACCCGCGGCCGCGCCACCATGAGAGAGCCAGAGGAGCTGATGCCAGAT
pTR-IRBP-RPGRsyn   (3601)  GTACCCGCGGCCGCGCCACCATGAGAGAGCCAGAGGAGCTGATGCCAGAT
                    3651                                                          3700
```

```
Contig sequence    (476)  AGCGGAGCAGTGTTTACCTTCGGAAAGTCCAAGTTCGCAGAGAATAACCC
pTR-IRBP-RPGRsyn  (3651)  AGCGGAGCAGTGTTTACCTTCGGAAAGTCCAAGTTCGCAGAGAATAACCC
                          3701                                            3750
Contig sequence    (526)  AGGAAAGTTCTGGTTTAAAAACGACGTGCCCGTCCACCTGTCTTGTGGCG
pTR-IRBP-RPGRsyn  (3701)  AGGAAAGTTCTGGTTTAAAAACGACGTGCCCGTCCACCTGTCTTGTGGCG
                          3751                                            3800
Contig sequence    (576)  ATGAGCATAGTGCCGTGGTCACTGGGAACAATAAGCTGTATATGTTCGGG
pTR-IRBP-RPGRsyn  (3751)  ATGAGCATAGTGCCGTGGTCACTGGGAACAATAAGCTGTATATGTTCGGG
                          3801                                            3850
Contig sequence    (626)  TCCAACAATTGGGGACAGCTGGGGCTGGGATCCAAATCTGCTATCTCTAA
pTR-IRBP-RPGRsyn  (3801)  TCCAACAATTGGGGACAGCTGGGGCTGGGATCCAAATCTGCTATCTCTAA
                          3851                                            3900
Contig sequence    (676)  GCCAACCTGCGTGAAGGCACTGAAACCCGAGAAGGTCAAACTGGCCGCTT
pTR-IRBP-RPGRsyn  (3851)  GCCAACCTGCGTGAAGGCACTGAAACCCGAGAAGGTCAAACTGGCCGCTT
                          3901                                            3950
Contig sequence    (726)  GTGGCAGAAACCACACTCTGGTGAGCACCGAGGGCGGGAATGTCTATGCC
pTR-IRBP-RPGRsyn  (3901)  GTGGCAGAAACCACACTCTGGTGAGCACCGAGGGCGGGAATGTCTATGCC
                          3951                                            4000
Contig sequence    (776)  ACCGGAGGCAACAATGAGGGACAGCTGGGACTGGGGGACACTGAGGAAAG
pTR-IRBP-RPGRsyn  (3951)  ACCGGAGGCAACAATGAGGGACAGCTGGGACTGGGGGACACTGAGGAAAG
                          4001                                            4050
Contig sequence    (826)  GAATACCTTTCACGTGATCTCCTTCTTTACATCTGAGCATAAGATCAAGC
pTR-IRBP-RPGRsyn  (4001)  GAATACCTTTCACGTGATCTCCTTCTTTACATCTGAGCATAAGATCAAGC
                          4051                                            4100
Contig sequence    (876)  AGCTGAGCGCCGGCTCCAACACATCTGCAGCCCTGACTGAGGACGGGCGC
pTR-IRBP-RPGRsyn  (4051)  AGCTGAGCGCCGGCTCCAACACATCTGCAGCCCTGACTGAGGACGGGCGC
                          4101                                            4150
Contig sequence    (926)  CTGTTCATGTGGGGAGATAATTCAGAGGGCCAGATTGGGCTGAAAAACGT
pTR-IRBP-RPGRsyn  (4101)  CTGTTCATGTGGGGAGATAATTCAGAGGGCCAGATTGGGCTGAAAAACGT
                          4151                                            4200
Contig sequence    (976)  GAGCAACGTGTGCGTGCCTCAGCAGGTGACCATCGGAAAGCCAGTCAGTT
pTR-IRBP-RPGRsyn  (4151)  GAGCAACGTGTGCGTGCCTCAGCAGGTGACCATCGGAAAGCCAGTCAGTT
                          4201                                            4250
Contig sequence   (1026)  GGATTTCATGTGGCTACTATCATAGCGCCTTCGTGACCACAGATGGCGAG
pTR-IRBP-RPGRsyn  (4201)  GGATTTCATGTGGCTACTATCATAGCGCCTTCGTGACCACAGATGGCGAG
                          4251                                            4300
Contig sequence   (1076)  CTGTACGTCTTTGGGGAGCCCGAAAACGGAAAACTGGGCCTGCCTAACCA
pTR-IRBP-RPGRsyn  (4251)  CTGTACGTCTTTGGGGAGCCCGAAAACGGAAAACTGGGCCTGCCTAACCA
                          4301                                            4350
Contig sequence   (1126)  GCTGCTGGGCAATCACCGGACACCCCAGCTGGTGTCCGAGATCCCTGAAA
pTR-IRBP-RPGRsyn  (4301)  GCTGCTGGGCAATCACCGGACACCCCAGCTGGTGTCCGAGATCCCTGAAA
                          4351                                            4400
Contig sequence   (1176)  AAGTGATCCAGGTCGCCTGCGGGGAGAGCATACAGTGGTCCTGACTGAG
pTR-IRBP-RPGRsyn  (4351)  AAGTGATCCAGGTCGCCTGCGGGGAGAGCATACAGTGGTCCTGACTGAG
                          4401                                            4450
Contig sequence   (1226)  AATGCCGTGTACACCTTCGGACTGGGCCAGTTTGGCCAGCTGGGGCTGGG
pTR-IRBP-RPGRsyn  (4401)  AATGCCGTGTACACCTTCGGACTGGGCCAGTTTGGCCAGCTGGGGCTGGG
                          4451                                            4500
Contig sequence   (1276)  AACCTTCCTGTTTGAGACATCCGAACCAAAAGTGATCGAGAACATTCGCG
pTR-IRBP-RPGRsyn  (4451)  AACCTTCCTGTTTGAGACATCCGAACCAAAAGTGATCGAGAACATTCGCG
                          4501                                            4550
Contig sequence   (1326)  ACCAGACTATCAGCTACATTTCCTGCGGAGAGAATCACACCGCACTGATC
pTR-IRBP-RPGRsyn  (4501)  ACCAGACTATCAGCTACATTTCCTGCGGAGAGAATCACACCGCACTGATC
                          4551                                            4600
Contig sequence   (1376)  ACAGACATTGGCCTGATGTATACCTTTGGCGATGGGCGGCACGGGAAGCT
pTR-IRBP-RPGRsyn  (4551)  ACAGACATTGGCCTGATGTATACCTTTGGCGATGGGCGGCACGGGAAGCT
                          4601                                            4650
Contig sequence   (1426)  GGGACTGGGCCTGGAGAACTTCACTAATCACTTCATCCCCACCCTGTGCT
pTR-IRBP-RPGRsyn  (4601)  GGGACTGGGCCTGGAGAACTTCACTAATCACTTCATCCCCACCCTGTGCT
                          4651                                            4700
Contig sequence   (1476)  CTAACTTCCTGCGGTTCATCGTGAAACTGGTCGCTTGCGGCGGGTGTCAC
```

FIG. 6 (Continued)

```
pTR-IRBP-RPGRsyn   (4651) CTAACTTCCTGCGGTTCATCGTGAAACTGGTCGCTTGCGGCGGGTGTCAC
                          4701                                           4750
Contig sequence    (1526) ATGGTGGTCTTCGCTGCACCTCATAGGGGCGTGGCTAAGGAGATCGAATT
pTR-IRBP-RPGRsyn   (4701) ATGGTGGTCTTCGCTGCACCTCATAGGGGCGTGGCTAAGGAGATCGAATT
                          4751                                           4800
Contig sequence    (1576) TGACGAGATTAACGATACATGCCTGAGCGTGGCAACTTTCCTGCCATACA
pTR-IRBP-RPGRsyn   (4751) TGACGAGATTAACGATACATGCCTGAGCGTGGCAACTTTCCTGCCATACA
                          4801                                           4850
Contig sequence    (1626) GCTCCCTGACTTCTGGCAATGTGCTGCAGAGAACCCTGAGTGCAAGGATG
pTR-IRBP-RPGRsyn   (4801) GCTCCCTGACTTCTGGCAATGTGCTGCAGAGAACCCTGAGTGCAAGGATG
                          4851                                           4900
Contig sequence    (1676) CGGAGAAGGGAGAGGGAACGCTCTCCTGACAGTTTCTCAATGCGACGAAC
pTR-IRBP-RPGRsyn   (4851) CGGAGAAGGGAGAGGGAACGCTCTCCTGACAGTTTCTCAATGCGACGAAC
                          4901                                           4950
Contig sequence    (1726) CCTGCCACCTATCGAGGGGACACTGGGACTGAGTGCCTGCTTCCTGCCTA
pTR-IRBP-RPGRsyn   (4901) CCTGCCACCTATCGAGGGGACACTGGGACTGAGTGCCTGCTTCCTGCCTA
                          4951                                           5000
Contig sequence    (1776) ACTCAGTGTTTCCACGATGTAGCGAGCGGAATCTGCAGGAGTCTGTCCTG
pTR-IRBP-RPGRsyn   (4951) ACTCAGTGTTTCCACGATGTAGCGAGCGGAATCTGCAGGAGTCTGTCCTG
                          5001                                           5050
Contig sequence    (1826) AGTGAGCAGGATCTGATGCAGCCAGAGGAACCCGACTACCTGCTGGATGA
pTR-IRBP-RPGRsyn   (5001) AGTGAGCAGGATCTGATGCAGCCAGAGGAACCCGACTACCTGCTGGATGA
                          5051                                           5100
Contig sequence    (1876) GATGACCAAGGAGGCCGAAATCGACAACTCTAGTACAGTGGAGTCCCTGG
pTR-IRBP-RPGRsyn   (5051) GATGACCAAGGAGGCCGAAATCGACAACTCTAGTACAGTGGAGTCCCTGG
                          5101                                           5150
Contig sequence    (1926) GCGAGACTACCGATATCCTGAATATGACACACATTATGTCACTGAACAGC
pTR-IRBP-RPGRsyn   (5101) GCGAGACTACCGATATCCTGAATATGACACACATTATGTCACTGAACAGC
                          5151                                           5200
Contig sequence    (1976) AATGAGAAGAGTCTGAAACTGTCACCAGTGCAGAAGCAGAAGAAACAGCA
pTR-IRBP-RPGRsyn   (5151) AATGAGAAGAGTCTGAAACTGTCACCAGTGCAGAAGCAGAAGAAACAGCA
                          5201                                           5250
Contig sequence    (2026) GACTATTGGCGAGCTGACTCAGGACACCGCCCTGACAGAGAACGACGATA
pTR-IRBP-RPGRsyn   (5201) GACTATTGGCGAGCTGACTCAGGACACCGCCCTGACAGAGAACGACGATA
                          5251                                           5300
Contig sequence    (2076) GCGATGAGTATGAGGAAATGTCCGAGATGAAGGAAGGCAAAGCTTGTAAG
pTR-IRBP-RPGRsyn   (5251) GCGATGAGTATGAGGAAATGTCCGAGATGAAGGAAGGCAAAGCTTGTAAG
                          5301                                           5350
Contig sequence    (2126) CAGCATGTGAGTCAGGGGATCTTCATGACACAGCCAGCCACAACTATTGA
pTR-IRBP-RPGRsyn   (5301) CAGCATGTGAGTCAGGGGATCTTCATGACACAGCCAGCCACAACTATTGA
                          5351                                           5400
Contig sequence    (2176) GGCTTTTTCAGACGAGGAAGTGGAGATCCCCGAGGAAAAAGAGGGCGCAG
pTR-IRBP-RPGRsyn   (5351) GGCTTTTTCAGACGAGGAAGTGGAGATCCCCGAGGAAAAAGAGGGCGCAG
                          5401                                           5450
Contig sequence    (2226) AAGATTCCAAGGGGAATGGAATTGAGGAACAGGAGGTGGAAGCCAACGAG
pTR-IRBP-RPGRsyn   (5401) AAGATTCCAAGGGGAATGGAATTGAGGAACAGGAGGTGGAAGCCAACGAG
                          5451                                           5500
Contig sequence    (2276) GAAAATGTGAAAGTCCACGGAGGCAGGAAGGAGAAAACAGAAATCCTGTC
pTR-IRBP-RPGRsyn   (5451) GAAAATGTGAAAGTCCACGGAGGCAGGAAGGAGAAAACAGAAATCCTGTC
                          5501                                           5550
Contig sequence    (2326) TGACGATCTGACTGACAAGGCCGAGGTGTCCGAAGGCAAGGCAAAATCTG
pTR-IRBP-RPGRsyn   (5501) TGACGATCTGACTGACAAGGCCGAGGTGTCCGAAGGCAAGGCAAAATCTG
                          5551                                           5600
Contig sequence    (2376) TCGGAGAGGCAGAAGACGGACCAGAGGGACGAGGGGATGGAACCTGCGAG
pTR-IRBP-RPGRsyn   (5551) TCGGAGAGGCAGAAGACGGACCAGAGGGACGAGGGGATGGAACCTGCGAG
                          5601                                           5650
Contig sequence    (2426) GAAGGCTCAAGCGGGGCTGAGCATTGGCAGGACGAGGAACGAGAGAAGGG
pTR-IRBP-RPGRsyn   (5601) GAAGGCTCAAGCGGGGCTGAGCATTGGCAGGACGAGGAACGAGAGAAGGG
                          5651                                           5700
Contig sequence    (2476) CGAAAAGGATAAAGGCCGCGGGGAGATGGAACGACCTGGAGAGGGCGAAA
pTR-IRBP-RPGRsyn   (5651) CGAAAAGGATAAAGGCCGCGGGGAGATGGAACGACCTGGAGAGGGCGAAA
```

FIG. 6 (Continued)

```
                         5701                                              5750
Contig sequence   (2526) AAGAGCTGGCAGAGAAGGAGGAATGGAAGAAAAGGGACGGCGAGGAACAG
pTR-IRBP-RPGRsyn  (5701) AAGAGCTGGCAGAGAAGGAGGAATGGAAGAAAAGGGACGGCGAGGAACAG
                         5751                                              5800
Contig sequence   (2576) GAGCAGAAAGAAAGGGAGCAGGGCCACCAGAAGGAGCGCAACCAGGAGAT
pTR-IRBP-RPGRsyn  (5751) GAGCAGAAAGAAAGGGAGCAGGGCCACCAGAAGGAGCGCAACCAGGAGAT
                         5801                                              5850
Contig sequence   (2626) GGAAGAGGGCGGCGAGGAAGAGCATGGCGAGGGAGAAGAGGAAGAGGGCG
pTR-IRBP-RPGRsyn  (5801) GGAAGAGGGCGGCGAGGAAGAGCATGGCGAGGGAGAAGAGGAAGAGGGCG
                         5851                                              5900
Contig sequence   (2676) ATAGAGAAGAGGAAGAGGAAAAAGAAGGCGAAGGGAAGGAGGAAGGAGAG
pTR-IRBP-RPGRsyn  (5851) ATAGAGAAGAGGAAGAGGAAAAAGAAGGCGAAGGGAAGGAGGAAGGAGAG
                         5901                                              5950
Contig sequence   (2726) GGCGAGGAAGTGGAAGGCGAGAGGGAAAAGGAGGAAGGAGAACGGAAGAA
pTR-IRBP-RPGRsyn  (5901) GGCGAGGAAGTGGAAGGCGAGAGGGAAAAGGAGGAAGGAGAACGGAAGAA
                         5951                                              6000
Contig sequence   (2776) AGAGGAAAGAGCCGGCAAAGAGGAAAAGGGCGAGGAAGAGGGCGATCAGG
pTR-IRBP-RPGRsyn  (5951) AGAGGAAAGAGCCGGCAAAGAGGAAAAGGGCGAGGAAGAGGGCGATCAGG
                         6001                                              6050
Contig sequence   (2826) GCGAAGGCGAGGAGGAAGAGACCGAGGGCCGCGGGGAAGAGAAAGAGGAG
pTR-IRBP-RPGRsyn  (6001) GCGAAGGCGAGGAGGAAGAGACCGAGGGCCGCGGGGAAGAGAAAGAGGAG
                         6051                                              6100
Contig sequence   (2876) GGAGGAGAGGTGGAGGGCGGAGAGGTCGAAGAGGGAAAGGGCGAGCGCGA
pTR-IRBP-RPGRsyn  (6051) GGAGGAGAGGTGGAGGGCGGAGAGGTCGAAGAGGGAAAGGGCGAGCGCGA
                         6101                                              6150
Contig sequence   (2926) AGAGGAAGAGGAAGAGGGCGAGGGCGAGGAAGAAGAGGGCGAGGGGGAAG
pTR-IRBP-RPGRsyn  (6101) AGAGGAAGAGGAAGAGGGCGAGGGCGAGGAAGAAGAGGGCGAGGGGGAAG
                         6151                                              6200
Contig sequence   (2976) AAGAGGAGGGAGAGGGCGAAGAGGAAGAGGGGGAGGGAAAGGGCGAAGAG
pTR-IRBP-RPGRsyn  (6151) AAGAGGAGGGAGAGGGCGAAGAGGAAGAGGGGGAGGGAAAGGGCGAAGAG
                         6201                                              6250
Contig sequence   (3026) GAAGGAGAGGAAGGGGAGGGAGAGGAAGAGGGGGAGGAGGGCGAGGGGGA
pTR-IRBP-RPGRsyn  (6201) GAAGGAGAGGAAGGGGAGGGAGAGGAAGAGGGGGAGGAGGGCGAGGGGGA
                         6251                                              6300
Contig sequence   (3076) AGGCGAGGAGGAAGAAGGAGAGGGGGAAGGCGAAGAGGAAGGCGAGGGGG
pTR-IRBP-RPGRsyn  (6251) AGGCGAGGAGGAAGAAGGAGAGGGGGAAGGCGAAGAGGAAGGCGAGGGGG
                         6301                                              6350
Contig sequence   (3126) AAGGAGAGGAGGAAGAAGGGGAAGGCGAAGGCGAAGAGGAGGGAGAAGGA
pTR-IRBP-RPGRsyn  (6301) AAGGAGAGGAGGAAGAAGGGGAAGGCGAAGGCGAAGAGGAGGGAGAAGGA
                         6351                                              6400
Contig sequence   (3176) GAGGGGAGGAAGAGGAAGGAGAAGGGAAGGGCGAGGAGGAAGGCGAAGA
pTR-IRBP-RPGRsyn  (6351) GAGGGGAGGAAGAGGAAGGAGAAGGGAAGGGCGAGGAGGAAGGCGAAGA
                         6401                                              6450
Contig sequence   (3226) GGGAGAGGGGGAAGGCGAGGAAGAGGAAGGCGAGGGCGAAGGAGAGGACG
pTR-IRBP-RPGRsyn  (6401) GGGAGAGGGGGAAGGCGAGGAAGAGGAAGGCGAGGGCGAAGGAGAGGACG
                         6451                                              6500
Contig sequence   (3276) GCGAGGGCGAGGGAGAAGAGGAGGAAGGGGAATGGGAAGGCGAAGAAGAG
pTR-IRBP-RPGRsyn  (6451) GCGAGGGCGAGGGAGAAGAGGAGGAAGGGGAATGGGAAGGCGAAGAAGAG
                         6501                                              6550
Contig sequence   (3326) GAAGGCGAAGGCGAAGGCGAAGAAGAGGGCGAAGGGGAGGGCGAGGAGGG
pTR-IRBP-RPGRsyn  (6501) GAAGGCGAAGGCGAAGGCGAAGAAGAGGGCGAAGGGGAGGGCGAGGAGGG
                         6551                                              6600
Contig sequence   (3376) CGAAGGCGAAGGGGAGGAAGAGGAAGGCGAAGGAGAAGGCGAGGAAGAAG
pTR-IRBP-RPGRsyn  (6551) CGAAGGCGAAGGGGAGGAAGAGGAAGGCGAAGGAGAAGGCGAGGAAGAAG
                         6601                                              6650
Contig sequence   (3426) AGGGAGAGGAGGAAGGCGAGGAGGAAGGAGAGGGGGAGGAGGAGGGAGAA
pTR-IRBP-RPGRsyn  (6601) AGGGAGAGGAGGAAGGCGAGGAGGAAGGAGAGGGGGAGGAGGAGGGAGAA
                         6651                                              6700
Contig sequence   (3476) GGCGAGGGCGAAGAAGAAGAAGAGGGAGAAGTGGAGGGCGAAGTCGAGGG
pTR-IRBP-RPGRsyn  (6651) GGCGAGGGCGAAGAAGAAGAAGAGGGAGAAGTGGAGGGCGAAGTCGAGGG
                         6701                                              6750
```

FIG. 6 (Continued)

```
Contig sequence   (3526)  GGAGGAGGGAGAAGGGGAAGGGGAGGAAGAAGAGGGCGAAGAAGAAGGCG
pTR-IRBP-RPGRsyn  (6701)  GGAGGAGGGAGAAGGGGAAGGGGAGGAAGAAGAGGGCGAAGAAGAAGGCG
                          6751                                          6800
Contig sequence   (3576)  AGGAAAGAGAAAAAGAGGGAGAAGGCGAGGAAAACCGGAGAAATAGGGAA
pTR-IRBP-RPGRsyn  (6751)  AGGAAAGAGAAAAAGAGGGAGAAGGCGAGGAAAACCGGAGAAATAGGGAA
                          6801                                          6850
Contig sequence   (3626)  GAGGAGGAAGAGGAAGAGGGAAAGTACCAGGAGACAGGCGAAGAGGAAAA
pTR-IRBP-RPGRsyn  (6801)  GAGGAGGAAGAGGAAGAGGGAAAGTACCAGGAGACAGGCGAAGAGGAAAA
                          6851                                          6900
Contig sequence   (3676)  CGAGCGGCAGGATGGCGAGGAATATAAGAAAGTGAGCAAGATCAAAGGAT
pTR-IRBP-RPGRsyn  (6851)  CGAGCGGCAGGATGGCGAGGAATATAAGAAAGTGAGCAAGATCAAAGGAT
                          6901                                          6950
Contig sequence   (3726)  CCGTCAAGTACGGCAAGCACAAAACCTATCAGAAGAAAAGCGTGACCAAC
pTR-IRBP-RPGRsyn  (6901)  CCGTCAAGTACGGCAAGCACAAAACCTATCAGAAGAAAAGCGTGACCAAC
                          6951                                          7000
Contig sequence   (3776)  ACACAGGGGAATGGAAAAGAGCAGCGAAGTAAAATGCCTGTGCAGTCAAA
pTR-IRBP-RPGRsyn  (6951)  ACACAGGGGAATGGAAAAGAGCAGCGAAGTAAAATGCCTGTGCAGTCAAA
                          7001                                          7050
Contig sequence   (3826)  ACGGCTGCTGAAGAATGGCCCAAGCGGGTCTAAAAAATTCTGGAACAATG
pTR-IRBP-RPGRsyn  (7001)  ACGGCTGCTGAAGAATGGCCCAAGCGGGTCTAAAAAATTCTGGAACAATG
                          7051                                          7100
Contig sequence   (3876)  TCCTGCCACACTATCTGGAACTGAAGTAAGCGGCCGCGCGGATCCAGACA
pTR-IRBP-RPGRsyn  (7051)  TCCTGCCACACTATCTGGAACTGAAGTAAGCGGCCGCGCGGATCCAGACA
                          7101                                          7150
Contig sequence   (3926)  TGATAAGATACATTGATGAGTTTGGACAAACCACAACTAGAATGCAGTGA
pTR-IRBP-RPGRsyn  (7101)  TGATAAGATACATTGATGAGTTTGGACAAACCACAACTAGAATGCAGTGA
                          7151                                          7200
Contig sequence   (3976)  AAAAAATGCTTTATTTGTGAAATTTGTGATGCTATTGCTTTATTTGTAAC
pTR-IRBP-RPGRsyn  (7151)  AAAAAATGCTTTATTTGTGAAATTTGTGATGCTATTGCTTTATTTGTAAC
                          7201                                          7250
Contig sequence   (4026)  CATTATAAGCTGCAATAAACAAGTTAACAACAACAATTGCATTCATTTTA
pTR-IRBP-RPGRsyn  (7201)  CATTATAAGCTGCAATAAACAAGTTAACAACAACAATTGCATTCATTTTA
                          7251                                     7292
Contig sequence   (4076)  TGTTTCAGGTTCAGGGGGAGGTGTGGGAGGTT---------------
pTR-IRBP-RPGRsyn  (7251)  TGTTTCAGGTTCAGGGGGAGGTGTGGGAGGTTTTTTAGCATC
```

FIG. 6 sequence alignment of the assembled contig obtained from sequencing of pTR-IRBP-RPGRsyn plasmid DNA to the reference pTR-IRBP-RPGRsyn sequence. The start and stop codons of rht RPGRsyn cDNA were bold and underlined.

FIG. 6 (Continued)

CODON OPTIMIZED NUCLEIC ACID ENCODING A RETINITIS PIGMENTOSA GTPASE REGULATOR (RPGR)

RELATED APPLICATIONS

This application claims the benefit of U.S. Provisional Application No. 61/979,633, filed on Apr. 15, 2014, the entire contents of which is expressly incorporated herein by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is "Sequence Listing" and is 16 kb in size.

FIELD OF THE INVENTION

This invention relates generally to codon optimized nucleic acid sequences encoding a human retinitis pigmentosa GTPase regulator (RPGR).

BACKGROUND OF THE INVENTION

Retinitis pigmentosa (RP) is an inherited degenerative disease of the retina that affects approximately one in 3,500 individuals, with an estimated 1.5 million patients worldwide. See Churchill et al., 2013, Invest. Ophthalmol. Vis. Sci. 54(2): 1411-1416. RP is caused by progressive loss of rod and cone photoreceptors, resulting in night blindness followed by loss of visual fields. The disease may result in legal or even complete blindness. Mutations in the retinitis pigmentosa GTPase regulator (RPGR) gene account for greater than 70% of the cases of human X-linked retinitis pigmentosa (XLRP), the most severe subtype of RP. See Beltran et al., 2012, PNAS 109(6): 2132-2137 and Bader et al., 2003, Invest. Ophthalmol. Vis. Sci. (44)4: 1458-1463.

Alternative splicing of the RPGR gene results in expression of multiple isoforms of the RPGR protein. The mRNA for isoform A contains all 19 exons of the gene, while the mRNA for isoform C contains exons 1 to 15 and a large part of intron 15. Intron 15 is a purine-rich region that contains highly repetitive sequences that code for glutamate and glycine repeats (EEEGEGEGE in human (SEQ ID NO: 9) and EEGEGE in mouse (SEQ ID NO: 10)), see Vervoort et al., Mutational hot spot within a new RPGR exon in X-linked retinitis pigmentosa. Nat Genet 2000; 25:462-6. Isoform A is constitutively expressed in all tissues while isoform C, which is also referred to as "ORF15", is the predominant form expressed in the connecting cilium of photoreceptor, see Hong et al., Invest Ophthalmol Vis Sci 2002; 43:3373-82, and Hong et al., Invest Ophthalmol Vis Sci 2003; 44:2413-21.

A total of 55% of RPGR-related XLRP is caused by mutations in ORF15, all of which result from deletions that lead to truncated proteins. Most of the other cases are caused by mutations in exons 1-13, which can be either missense or nonsense mutations, with a small number caused by mutations in introns or large deletions. No cases have been identified due to mutations in exons 16 to 19.

Recent studies have demonstrated the potential of gene therapy approaches to treating XLRP caused by mutations in the RPGR gene. For example, Beltran et al. have shown that subretinal injections of adeno-associated virus (AAV) vectors expressing human RPGR increased rod and cone photoreceptor function in a canine model of XLRP.

However one of the challenges in large-scale production of AAV vectors for clinical use is that nucleic acid sequences encoding a protein of interest such as RPGR may be unstable, resulting in the accumulation of several mutations and deletions. For example, the RPGR gene contains a region of 1.2 kb called ORF15 near the 3' end of the cDNA that is highly repetitive and GA rich. This region is a mutation "hot spot" in population. This repetitive region is very unstable during cloning and vector preparation and clones obtained generally contain mutations and deletions. These mutations can potentially alter or eliminate RPGR protein function, limiting the use of this protein in gene therapy applications. Therefore a need exists to identify methods of stabilizing RPGR cDNAs during large-scale production of AAV vectors.

SUMMARY OF THE INVENTION

It has been surprisingly found that the nucleic acid sequence of SEQ ID NO: 1 encoding the human RPGR protein is stable in large scale production of AAV plasmid pTR-IRBP-RPGRsyn. This nucleic acid sequence was developed through codon optimization of the wild type RPGR cDNA. In one aspect, the present invention provides a polynucleotide comprising the nucleic acid sequence of SEQ ID NO: 1 encoding a human RPGR protein.

In one aspect, the invention features a polynucleotide comprising the nucleic acid sequence of SEQ ID NO: 1 encoding a human retinitis pigmentosa GTPase regulator (RPGR) protein.

In one embodiments, the invention features an expression cassette comprising the polynucleotide of the above aspect, and an expression control sequence operably linked and heterologous to the nucleic acid sequence.

In another embodiment, the invention features a vector comprising the polynucleotide of claim 1. In a further embodiment, the vector is a recombinant adeno-associated (rAAV) expression vector.

In another embodiment, the invention features a recombinant herpes simplex virus (rHSV) comprising the polynucleotide of any one of the above aspects.

In another embodiment, the invention features a host cell comprising the polynucleotide of any one of the above aspects. In a related embodiment, the host cell is a mammalian cell. In a further related embodiment, the host cell is a HeLa cell, a BHK21 cell or a Vero cell. In another further embodiment, the host cell is a V27 cell.

In another embodiment, the expression control sequence is a human interphotoreceptor retinoid-binding protein (IRBP) promoter. In a further related embodiment, the human IRBP promoter comprises a nucleic acid sequence having at least 95% sequence identity to the nucleic acid sequence of SEQ ID NO: 8 and directs preferential expression in rods and cones. In another further embodiment, the human IRBP promoter comprises the nucleic acid sequence of SEQ ID NO: 8.

In one embodiment, the polynucleotide comprises the nucleic acid sequence of SEQ ID NO: 7.

The invention also features in another embodiment a method of producing the rAAV expression vector of the above aspect, comprising (a) infecting a host cell with a recombinant herpes simplex virus (rHSV) comprising the nucleic acid sequence of SEQ ID NO: 1; (b) incubating the host cell; and (c) following incubation, collecting rAAV from the host cell of step (b).

In one embodiment, the host cell is a HeLa cell, a BHK21 cell or a Vero cell.

In another embodiment, the rHSV further comprises a human IRBP promoter operably linked to the nucleic acid sequence of SEQ ID NO: 1. In a further embodiment, the human IRBP promoter comprises a nucleic acid sequence having at least 95% sequence identity to the nucleic acid sequence of SEQ ID NO: 8 and directs preferential expression in rods and cones. In a further related embodiment, the human IRBP promoter comprises the nucleic acid sequence of SEQ ID NO: 8.

In another embodiment, the rHSV comprises the nucleic acid sequence of SEQ ID NO: 7.

BRIEF DESCRIPTION OF THE DRAWINGS

FIGS. 1A-1B show a sequence alignment of codon optimized RPGR cDNA (RPGRsyn; SEQ ID NO: 1) and the wildtype RPGR cDNA (Genbank Accession No. NM_001034853; SEQ ID NO: 5).

FIG. 6 shows the restriction maps of pTR-IRBP-RPGRsyn plasmid DNA isolated from transformed bacteria after 4 rounds of serial overnight propagation, along with a control plasmid of pTR-IRBP-CNGB3co. Bacteria transformed with pTR-IRBP-RPGRsyn or pTR-IRBP/GNAT2-hCNGB3co plasmids were grown in medium at 37° C., overnight. In the next morning, plasmid DNA was purified from 1.5 mL of overnight culture, and the remaining culture was left at room temperature until late afternoon and then used to inoculate 2 mLs of culture medium (1:1000 dilution) for the $2^{nd}$ round propagation. Same procedures were followed for the $3^{rd}$ and $4^{th}$ round of propagation. Plasmid DNA purified from each round were then analyzed by restriction digestion with Sma I to confirm the integrity of the ITR sequence of the plasmid. Restriction maps kept same for both pTR-IRBP-RPGRsyn and the control plasmid pTR-IRBP-CNGB3co, through the 3 rounds of propagation in bacteria. However, the yield was significantly decreased after $3^{rd}$ round propagation and almost no plasmid restriction fragments were detected after $4^{th}$ round propagation in bacteria. FIG. 6 discloses SEQ ID NOS 11 and 12, respectively, in order of appearance.

DETAILED DESCRIPTION OF THE INVENTION

Figure 2:
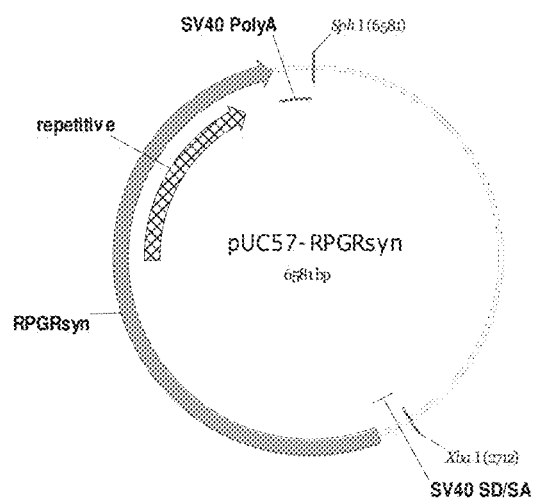
FIG. 2 shows a map of plasmid pUC57-RPGRsyn.

The invention provides a polynucleotide comprising the nucleic acid sequence of SEQ ID NO: 1 encoding a human retinitis pigmentosa GTPase regulator (RPGR) protein. The nucleic acid sequence has been codon optimized for enhanced stability during vector replication, and may be used, for example, for production of adeno-associated virus (AAV) vectors for gene therapy applications.

Nucleic acid sequences may be codon optimized to improve stability or heterologous expression in host cells without changing the encoded amino acid sequence. For example, codon optimization may be used to remove sequences that negatively impact gene expression, transcript stability, protein expression or protein stability, such as transcription splice sites, DNA instability motifs, polyadenylation sites, secondary structure, AU-rich RNA elements, secondary ORFs, codon tandem repeats, or long range repeats. Codon optimization may also be used to adjust the G/C content of a sequence of interest.

A codon consists of a set of three nucleotides and encodes a specific amino acid or results in the termination of translation (i.e. stop codons). The genetic code is redundant in that multiple codons specify the same amino acid, i.e., there are a total of 61 codons encoding 20 amino acids. Codon optimization replaces codons present in a DNA sequence with preferred codons encoding the same amino acid, for example, codons preferred for mammalian expression. Thus, the amino acid sequence is not altered during the process. Codon optimization can be performed using gene optimization software. The codon optimized nucleotide sequence is translated and aligned to the original protein sequence to ensure that no changes were made to the amino acid sequence. For example, the nucleotide sequence of SEQ ID NO: 1 encoding human RPGR is a codon optimized version of the wild type human RPGR nucleotide sequence (Genbank Accession No. NM_001034853, SEQ ID NO: 5). Both SEQ ID NO: 1 and SEQ ID NO: 5 encode the same RPGR protein (SEQ ID NO: 6).

Methods of codon optimization are known in the art and are described, for example, in U.S. Application Publication No. 2008/0194511 and U.S. Pat. No. 6,114,148.

The nucleic acid sequences of the present invention can be made as synthetic sequences. Techniques for constructing synthetic nucleic acid sequences are known in the art, and synthetic gene sequences may be purchased from several companies, including DNA 2.0 (Menlo Park, Calif.) and GenScript USA Inc. (Piscataway, N.J.). Alternatively, codon changes can be introduced by standard molecular biology techniques such as site-specific in vitro mutagenesis, PCR, or any other genetic engineering methods known in art which are suitable for specifically changing a nucleic acid sequence. In vitro mutagenesis protocols are described, for example, in In Vitro Mutagenesis Protocols, Braman, ed., 2002, Humana Press, and in Sankaranarayanan, Protocols in Mutagenesis, 2001, Elsevier Science Ltd.

The human RPGR gene is located in chromosomal region Xp21.1 and spans 172 kb. Shu et al., 2012, Invest. Ophthalmol. Vis. Sci. 53(7): 3951-3958. There are multiple alternatively spliced transcripts, all of which encode an amino (N)-terminal RCC1-like (RCCL) domain. The RCCL domain is structurally similar to the RCC1 protein, a guanine nucleotide exchange factor for the small guanosine triphosphate-binding protein, Ran. The RPGR gene contains 19 exons (RPGRex1-19), encoding a predicted 90 kDa protein. Exons 2 to 11 encode the RCCL domain, whereas exons 12 to 19 encode a carboxyl (C)-terminal domain rich in acidic residues and ending in an isoprenylation anchorage signal. Mutations found in RPGRex1-19 account for 15% to 20% of XLRP patients, and subsequent studies revealed many more disease-causing mutations within one or more transcripts containing an alternatively spliced C-terminal exon called ORF15 (RPGRORF15). A high frequency of microdeletions, frameshift, and premature stop mutations are found within the ORF15.

In one embodiment, the RPGR cDNA used for codon optimization is the full-length human RPGRORF15 clone, variant C, Genbank Accession No. NM_001034853 (SEQ ID NO: 5). See Vervoort et al., 2000, Nat Genet 25: 462-466. This clone contains exons 1-ORF15 and was generated using three-way ligation by step-wise amplifying exons 1-part of 15b (nucleotides 169-1990) from human lymphocytes and 1991-3627 from human genomic DNA. See Beltran et al., 2012, PNAS 109(6): 2132-2137.

RPGR is widely expressed and shows a complex expression pattern. See Shu et al., cited above. RPGR transcripts are detected in different tissues, including brain, eye, kidney, lung, and testis in several different species. RPGR protein is detected in retina, trachea, brain, and testis. In human, mouse, and bovine retina, RPGR mainly localizes to photoreceptor connecting cilia, but expression has also been reported in outer segments in some species. RPGR is expressed in the transitional zone of motile cilia and within human and monkey cochlea.

The invention also provides an expression cassette comprising the nucleic acid sequence of SEQ ID NO: 1 and an expression control sequence operably linked and heterologous to the nucleic acid sequence. The term "expression control sequence" refers to any genetic element (e.g., polynucleotide sequence) that can exert a regulatory effect on the replication or expression (transcription or translation) of the nucleic acid sequence. Common expression control sequences include promoters, polyadenylation signals, transcription termination sequences, upstream regulatory domains, origins of replication, internal ribosome entry sites (IRES), and enhancers.

An expression control sequence is operably linked with a nucleic acid sequence when the expression control sequence is placed in a functional relationship with the second nucleic acid sequence. For example, a promoter is operably linked to a coding sequence if the promoter affects the expression of the coding sequence. The term operably linked encompasses, for example, an arrangement of an expression control sequence with the nucleic acid sequence to be expressed and optionally further expression control sequences, such as a terminator or enhancer, such that each of the expression control sequences can allow, modify, facilitate or otherwise influence expression of the nucleic acid sequence.

The term "heterologous" refers to nucleic acid or amino acid sequences that are obtained or derived from different source organisms or from different genes or proteins within the same source organism. For example, an expression control sequence that is not a native expression control sequence of the human RPGR gene is considered to be heterologous to the human RPGR gene. In certain embodiments, the expression control sequence is a promoter that is heterologous to the RPGR gene.

In a preferred embodiment, the expression control sequence is a human interphotoreceptor retinoid-binding protein (IRBP) promoter. IRBP is a large glycoprotein that is expressed only in the photoreceptor cells of the retina and to a much lesser extent in pinealocytes in the pineal gland in the brain. See Al-Ubaidi et al., 1992, J Cell Biology, 119(6) 1681-1687. The IRBP promoter region is well characterized. For example, Albini et al. (1990, Nucleic Acids Research 18(17): 5181-5187) describe a nucleotide sequence of the human IRBP promoter region (Genbank Accession No. X53044) containing 2818 bp of the 5' untranscribed region (SEQ ID NO: 2). Beltran et al. (cited above) demonstrated that a 235 bp fragment of the human IRBP promoter directed GFP expression in both rods and cones of normal canine retina in a dose- and time-dependent manner. A 1.3 kb fragment of the 5' untranslated region of the human IRBP gene (SEQ ID NO: 3) directed expression of a bacterial reporter gene (chloramphenicol acetyltransferase, CAT) specifically to photoreceptor cells in transgenic mice. See Al Ubaidi et al. 1992, J Cell Biology 119: 1681-1687. Nested deletion analysis of a 1783 bp fragment of the mouse IRBP 5' flanking region indicated that high promoter activity was maintained with a fragment consisting of 70 bp 5' to the transcription start site (SEQ ID NO: 4), but that elements upstream of this 70 bp fragment are required for complete tissue-specific regulation. See Boatright, et al., 1997, Molecular Vision 3: 15.

In a preferred embodiment, the human IRBP promoter comprises a nucleic acid sequence having at least 95%, 96%, 97%, 98% or 99% sequence identity to SEQ ID NO: 2, SEQ ID NO: 3, SEQ ID NO: 4, or SEQ ID NO: 8. In a further preferred embodiment, the human IRBP promoter comprises SEQ ID NO: 8.

As used herein, the term "vector" refers to a nucleic acid molecule capable of transporting another nucleic acid to which it has been linked, e.g., a plasmid. Preferred vectors are those capable of autonomous replication and/or expression of nucleic acids to which they are linked. An "rAAV vector" is a recombinant vector that includes nucleic acid sequences derived from adeno-associated virus (AAV). Recombinant AAV is produced in vitro by introduction of gene constructs into cells known as producer cells. Recombinant AAV has been studied extensively as a vehicle for gene therapy and for its potential applicability as a treatment for human diseases based on genetic defects. At the clinical level, the rAAV vector has been used in human clinical trials to deliver the cftr gene to cystic fibrosis patients and the Factor IX gene to hemophilia patients (Flotte, et al., 1998, Methods Enzymol 292:717-732; and Wagner et al., 1998, Lancet 351:1702-1703). Systems for production of rAAV employ three elements: 1) a gene cassette containing the gene of interest, 2) a gene cassette containing AAV rep and cap genes and 3) a source of "helper" virus proteins. Methods of producing rAAV are known in the art and are described, for example, in U.S. Pat. No. 7,091,029.

Production of rAAV vectors for gene therapy is carried out in vitro, using suitable producer cell lines. A preferred cell line is 293, but production of rAAV can be achieved using other cell lines, including but not limited to human or monkey cell lines such as Vero, WI 38 and HeLa, and rodent cells, such as BHK cells, e.g. BHK21.

In particular embodiments, the rAAV comprises the nucleic acid sequence of SEQ ID NO: 1 encoding the human RPGR protein. The rAAV may further comprise one or more expression control sequences operably linked to the nucleic acid sequence of SEQ ID NO: 1. In a preferred embodiment, the expression control sequence is a human IRBP promoter. In a further preferred embodiment, the human IRBP promoter comprises a nucleic acid sequence having at least 95%, 96%, 97%, 98% or 99% sequence identity to the nucleic acid sequence of SEQ ID NO: 2, SEQ ID NO: 3, SEQ ID NO: 4, or SEQ ID NO: 8 and directs preferential expression in rods and cones. In a particularly preferred embodiment, the human IRBP promoter comprises SEQ ID NO: 8.

In certain embodiments, the rAAV further comprises an SV40 poly A tail, an SV40 splice donor/splice acceptor (SD/SA) sequence, and a Kozak sequence, each operably linked to the nucleic acid sequence of SEQ ID NO: 1. In a preferred embodiment, the rAAV comprises the nucleic acid sequence of SEQ ID NO: 7.

One strategy for delivering all of the required elements for rAAV production to the producer cell line involves transfecting the cells with plasmids containing gene cassettes encoding the necessary gene products, as well as infection of the cells with the helper virus Ad to provide the helper functions. This system employs plasmids with two different gene cassettes. The first is a proviral plasmid encoding the recombinant DNA to be packaged as rAAV. The second is a plasmid encoding the rep and cap genes. Other DNA viruses, such as Herpes simplex virus type 1 (HSV-1) can be used instead of Ad to provide helper virus gene products needed for rAAV production (Conway et al., 1999, Gene Ther. 6:973-985).

Another strategy for rAAV production is based on the use of two or more recombinant rHSV-1 viruses to simultaneously co-infect producer cells with all of the components necessary for producing rAAV. This strategy employs at least two different forms of rHSV, each containing a different gene cassette. In addition to supplying the necessary helper functions, each of these rHSV viruses is engineered to deliver different AAV (and other) genes to the producer cells upon infection. The two rHSV forms are referred to as the "rHSV/rc virus" and the "rHSV expression virus." The rHSV/rc virus contains a gene cassette in which the rep and cap genes from AAV are inserted into the HSV genome. The rep genes are responsible for replication and packaging of the rAAV genome in host cells infected with AAV. The cap genes encode proteins that comprise the capsid of the rAAV produced by the infected cells.

The second recombinant HSV is an "rHSV expression virus." A usual element of an rAAV production system is an expression cassette containing transgene DNA sequences encoding a gene(s) of interest, such as the RPGR gene, along with promoter elements necessary for expression of the gene. In particular embodiments, the rHSV comprises the nucleic acid sequence of SEQ ID NO: 1 encoding the human RPGR protein. Expression vectors engineered for rAAV production are generally constructed with the gene of interest inserted between two AAV-2 inverted terminal repeats (ITRs). The ITRs are responsible for the ability of native AAV to insert its DNA into the genome of host cells upon infection or otherwise persist in the infected cells. The expression cassette is incorporated into the rHSV expression virus described above. This second rHSV virus is used for simultaneous co-infection of the cells along with the rHSV-1/rc virus.

The terms "recombinant HSV," "rHSV," "rHSV vector," and "rHSV expression vector" refer to isolated, genetically modified forms of herpes simplex virus (HSV) containing heterologous genes incorporated into the viral genome. Methods for production of rHSV are known in the art and are described, for example, by Conway et al. (1999, Gene Ther. 6:973-985); Conway et al. (1997, J Virol 71: 8780-8789) and U.S. Pat. No. 7,037,723.

In particular embodiments, the rHSV comprises the nucleic acid sequence of SEQ ID NO: 1 encoding the human RPGR protein. The rHSV may further comprise one or more expression control sequences for regulating expression of the nucleic acid sequence of SEQ ID NO: 1, wherein the expression control sequence is operably linked to the nucleic acid sequence of SEQ ID NO: 1. In a preferred embodiment, the expression control sequence is a human IRBP promoter that is operably linked to the nucleic acid sequence of SEQ ID NO: 1. In a further preferred embodiment, the human IRBP promoter comprises a nucleic acid sequence having at least 95%, 96%, 97%, 98% or 99% sequence identity to the nucleic acid sequence of SEQ ID SEQ ID NO: 2, SEQ ID NO: 3, SEQ ID NO: 4, or SEQ ID NO: 8 and directs preferential expression in rods and cones. In a particularly preferred embodiment, the human IRBP promoter comprises SEQ ID NO: 8.

In certain embodiments of the aforementioned methods, the rHSV further comprises an SV40 poly A tail, an SV40 splice donor/splice acceptor (SD/SA) sequence, and a Kozak sequence, each operably linked to the nucleic acid sequence of SEQ ID NO: 1. In a preferred embodiment, the rHSV comprises the nucleic acid sequence of SEQ ID NO: 7.

The invention also provides a method of producing an rAAV expression vector comprising a polynucleotide comprising the nucleic acid sequence of SEQ ID NO: 1 encoding a human RPGR protein. In one embodiment, the method comprises (a) infecting a host cell with a recombinant herpes simplex virus (rHSV) comprising the nucleic acid sequence of SEQ ID NO: 1; (b) incubating the host cell; and (c) following incubation, collecting rAAV from the host cell of step (b).

Methods of producing rAAV expression vectors by infecting a host cell with an rHSV are known in the art and are described for example in U.S. Pat. No. 7,091,029. For example, in one embodiment, the host cells are infected with rHSV by diluting the virus in growth medium such as DMEM and adding the virus to flasks containing the host cells. The host cells may be incubated with the virus for various intervals, for example, 22, 26, 30, 34, or 46 hours. Following the incubation interval, the virus-infected cells may be harvested by pelleting, followed by resuspension in DMEM. Cell-associated rAAV may be collected from the host cells by lysis of the cells using standard techniques involving three rounds of freezing and thawing (See Conway et al., 1999, cited above).

In particular embodiments, the host cell used for producing an rAAV expression vector in the aforementioned methods is a HeLa cell, a BHK21 cell or a Vero cell.

The rHSV used in the aforementioned method may further comprise one or more expression control sequences for regulating expression of the nucleic acid sequence of SEQ ID NO: 1 that is operably linked to the nucleic acid sequence of SEQ ID NO: 1. In a preferred embodiment, the expression control sequence is a human IRBP promoter that is operably linked to the nucleic acid sequence of SEQ ID NO: 1. In a further preferred embodiment, the human IRBP promoter comprises a nucleic acid sequence having at least 95%, 96%, 97%, 98% or 99% sequence identity to the nucleic acid sequence of SEQ ID NO: 2, SEQ ID NO: 3, SEQ ID NO: 4, or SEQ ID NO: 8 and directs preferential expression in rods and cones. In a particularly preferred embodiment, the human IRBP promoter comprises SEQ ID NO: 8.

In certain embodiments of the aforementioned methods, the rHSV further comprises an SV40 poly A tail, an SV40 splice donor/splice acceptor (SD/SA) sequence, and a Kozak sequence, each operably linked to the nucleic acid sequence of SEQ ID NO: 1. In a preferred embodiment, the rHSV comprises the nucleic acid sequence of SEQ ID NO: 7.

Description of Sequences

| SEQ ID NO: | Description |
|---|---|
| 1 | Codon modified RPGR cDNA |
| 2 | Human IRBP promoter, 2818 bp. Albini et al., 1990, Nuc Acid Res 18: 5181-5187). SEQ ID NO: 2 comprises SEQ ID NO: 3 and 4. |
| 3 | Human IRBP promoter, 1326 bp. Al Ubaidi et al. 1992, J Cell Biology 119: 1681-1687 |
| 4 | Mouse IRBP core promoter region, 70 bp. Boatright, et al., 1997, Molecular Vision 3: 15. |
| 5 | Wildtype RPGR cDNA, Genbank Accession No. NM_001034853 |
| 6 | Wildtype RPGR amino acid sequence |
| 7 | 3871 bp synthesized sequence comprising SEQ ID NO: 1, an SV40 poly A tail, the SV40 SD/SA sequence, Kozak sequence, and restriction sites |
| 8 | Human IRBP promoter, 234 bp fragment used in the RPGRsyn expression cassette |

The following examples serve to illustrate certain embodiments and aspects of the present invention and are not to be construed as limiting the scope of the invention.

EXAMPLES

Example 1

Codon Optimization of the RPGR Gene and Evaluation of Plasmid Stability

A wildtype RPGR cDNA in an AAV plasmid used for AAV manufacturing was found to contain several mutations and deletions in the region from nt 2461 to nt 3057. There were a total of 42 bp accumulated deletions or substitutions across this region. The plasmid clone was found to be stable during plasmid propagation in bacteria, and no sequence changes were found in the AAV vector.

Figure 1A:
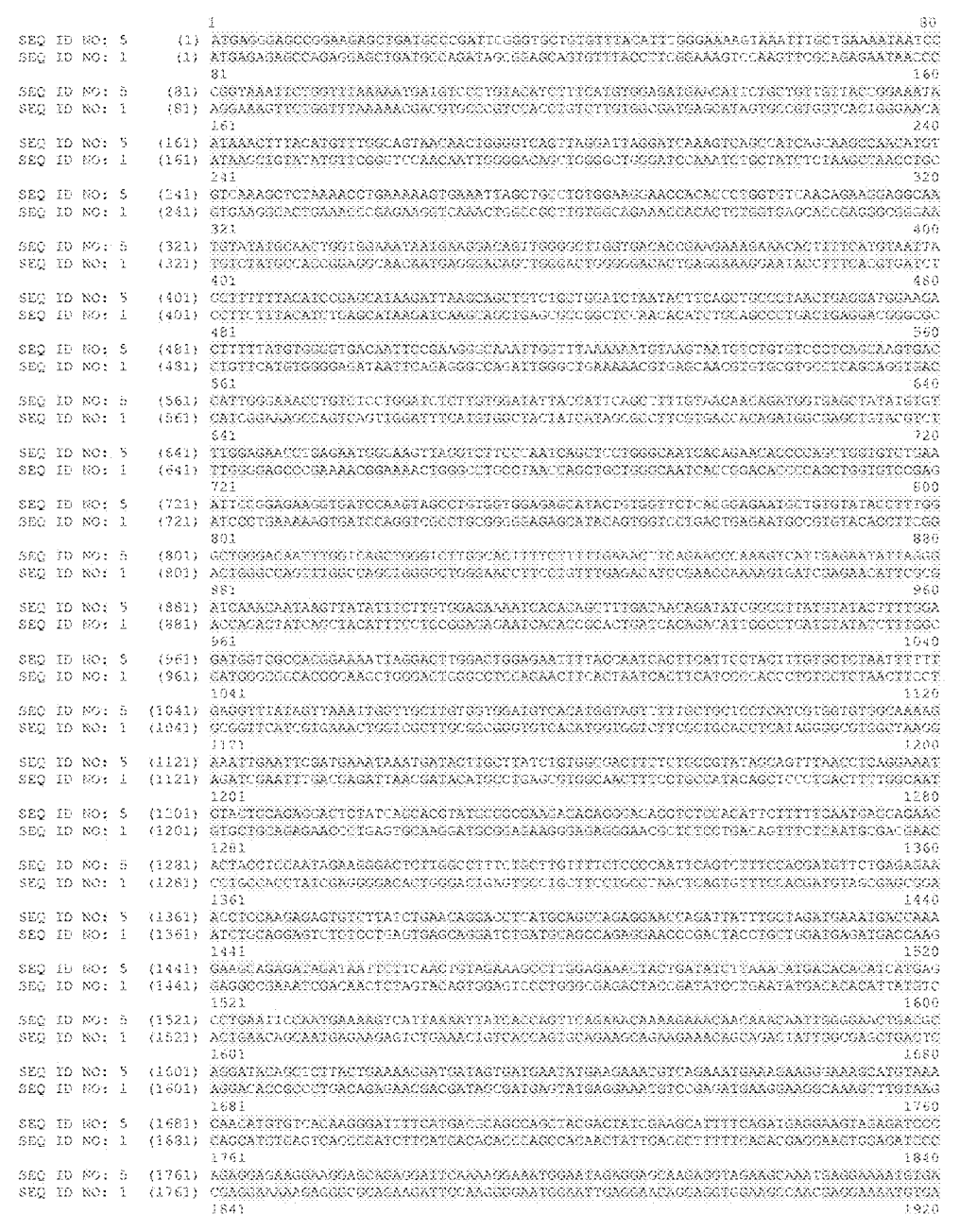
Figure 1B:
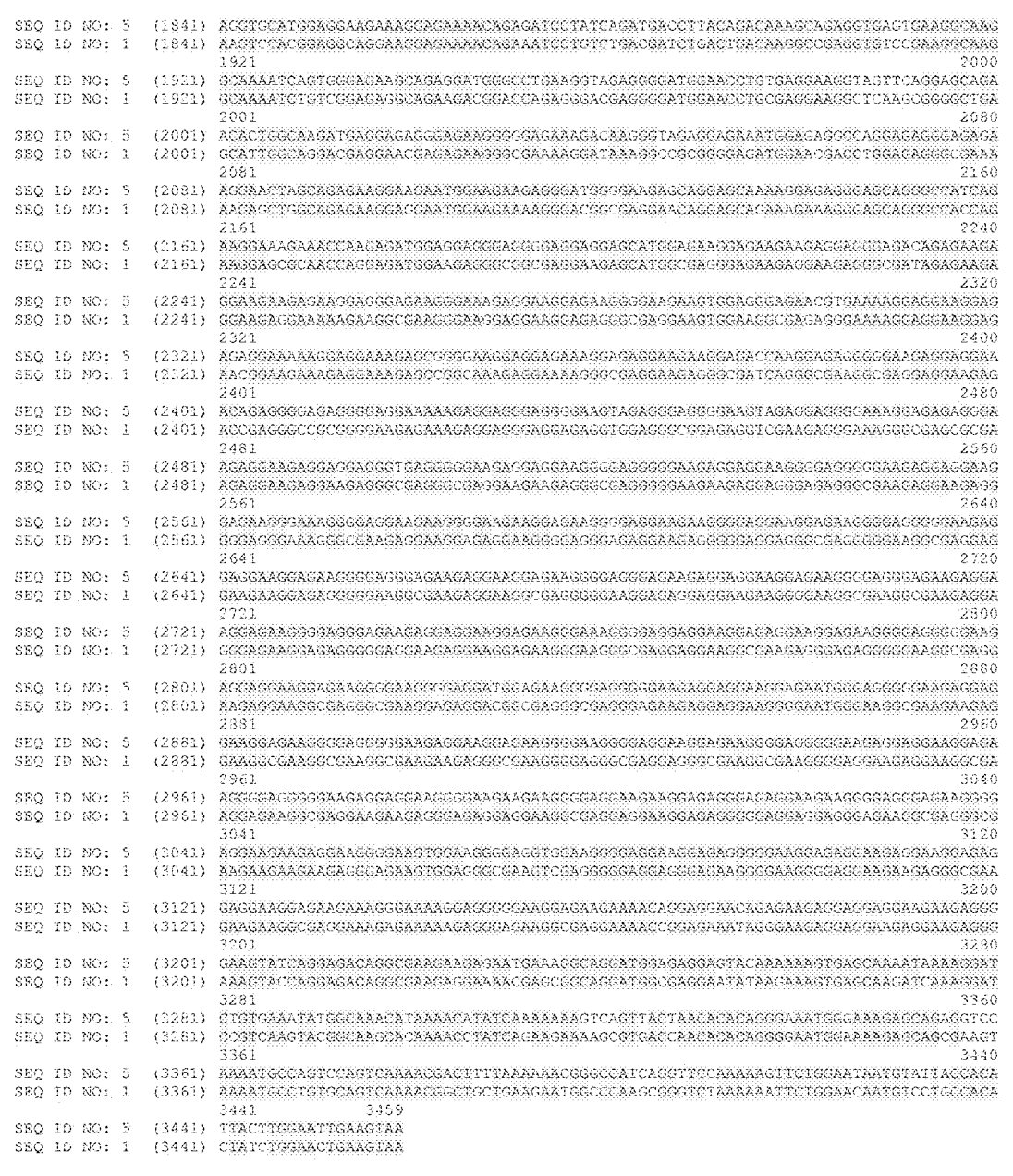

A 3459 bp coding sequence of the RPGR gene, variant C (SEQ ID NO: 5) was codon-optimized at Genscript, Inc. for mammalian expression. Codon optimization was used both to select codons of high frequency in mammals and to alter GC content to enhance stability, and to reduce the repetitive nature of the gene. The codon optimized version of the RPGR coding sequence (RPGRsyn; SEQ ID NO: 1) shares 72.1% sequence identity with the original gene (SEQ ID NO: 5). See FIG. 1. The codon optimized gene encodes the same polypeptide as the original gene, i.e. the polypeptide of SEQ ID NO: 6. The RPGRsyn gene was synthesized at GenScript along with an SV40 poly A tail, the SV40 SD/SA sequence, a Kozak sequence, and restriction sites for cloning purposes. The entire 3871 bp synthesized sequence is provided as SEQ ID NO: 7.

Figure 3:
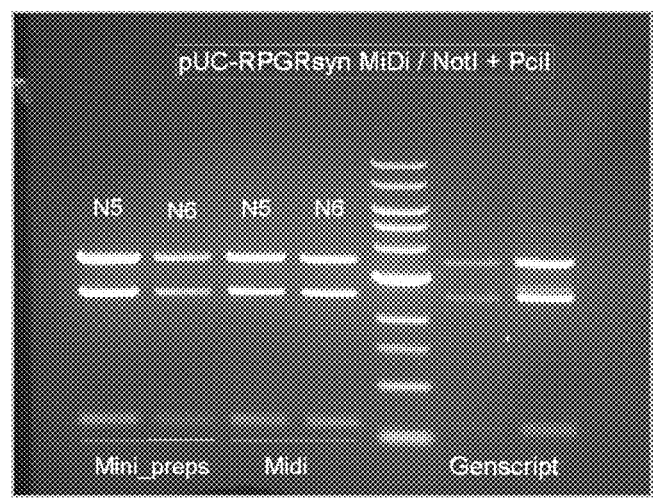
FIG. 3 shows pUC57-RPGRsyn plasmid DNA clones N5 and N6 prepared by mini-prep and larger scale midi-prep (Midi) and digested with restriction enzymes NotI and PciI. Plasmid DNA from mini-preps was retransformed into SURE2 cells before larger scale production by midi-prep.
Figure 4:
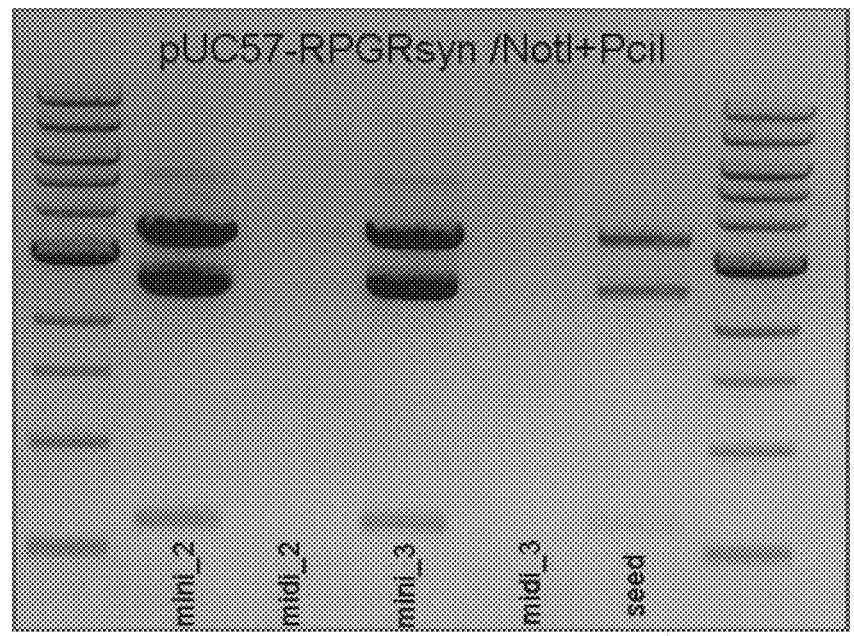
FIG. 4 shows pUC57-RPGRsyn plasmid DNA from mini-preps (mini_2 and mini_3) digested with restriction enzymes NotI and PciI. Plasmid DNA was not detectable in larger scale midi preps (midi_2 and midi_3). Seeding culture was stored at 4° C. overnight and used as the inoculant for larger scale plasmid production.
Figure 5:
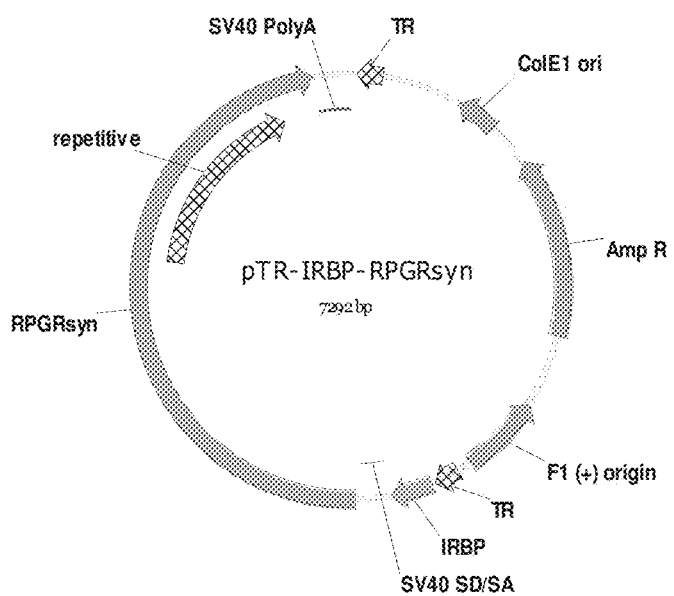
FIG. 5 shows a map of AAV proviral plasmid pTR-IRBP-RPGRsyn
Figure 7:
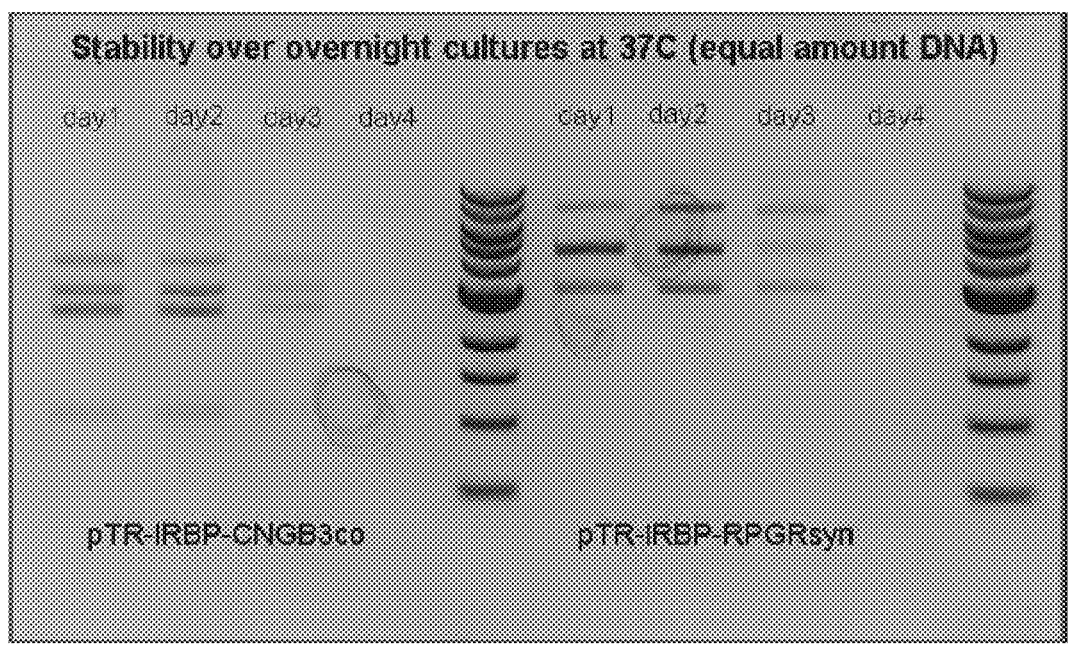
FIG. 7 shows the sequence alignment of the consensus sequence of contigs obtained from pTR-IRBP-RPGRsyn plasmid DNA to the reference pTR-IRBP-RPGRsyn sequence.

A map of the plasmid containing RPGRsyn (pUC57-RPGRsyn) is shown in FIG. 2. This plasmid was able to propagate stably in bacteria in small scale plasmid production. This plasmid also maintained its stability in larger scale production after being retransformed into SURE2 cells, a bacteria strain used for cloning of the AAV plasmid. See FIG. 3. Clone N5 of the pUC57-RPGRsyn plasmid DNA produced in large scale production was confirmed to be identical to the original plasmid by DNA sequencing. The plasmid yield could range from very low yield to none at all if the seeding culture was stored at 4° C. overnight and used as the inoculant for large scale plasmid production. See FIG. 4. The RPGRsyn cDNA was then released from pUC57-RPGRsyn plasmid and inserted into a pTR containing plasmid to generate the AAV proviral plasmid pTR-IRBP-RPGRsyn (FIG. 5). pTR-IRBP-RPGRsyn contains inverted terminal repeats (ITR) of AAV2 and IRBP promoter. Large scale production of the plasmid confirmed to be 100% correct upon DNA sequencing (FIG. 6). To further confirm the stability of pTR-IRBP-RPGRsyn, bacteria transformed with pTR-IRBP-RPGRsyn or pTR-IRBP/GNAT2-hCNGB3co plasmids were grown in medium at 37° C., overnight. In the next morning, plasmid DNA was purified from 1.5 mL of overnight culture, and the remaining culture was left at room temperature until late afternoon and then used to inoculate 2 mLs of culture medium (1:1000 dilution) for the $2^{nd}$ round propagation. Same procedures were followed for the $3^{rd}$ and $4^{th}$ round propagation. Plasmid DNA purified from each round was then analyzed by restriction digestion with Sma I to confirm the integrity of the ITR sequence of the plasmid. As shown in FIG. 6, the yield of pTR-IRBP-RPGRsyn declined during the serial passages; however, the same pattern is observed for pTR-IRBP-CNGB3co, a plasmid that contains the stable hCNGB3 cDNA. Therefore, the decline of plasmid yield is related to bacteria itself or other features such as TR, but not to the RPGRsyn. Also noted in FIG. 7, the 4.2 kb band containing RPGRsyn has been stable over the passages (it will become loose or smear if unstable).

Example 2

Construction of AAV Plasmids and Evaluation in Bacteria

An AAV plasmid (pTR-IRBP-RPGRsyn) comprising an RPGRsyn expressing cassette comprising the IRBP promoter (234 bp), the RPGRsyn cDNA (SEQ ID NO: 1), and an SV40 polyA signal sequence is constructed. This IRBP fragment is contained within the 235 bp fragment used by Beltran et al. in the canine model (See Beltran et al., 2012, PNAS 109(6): 2132-2137). After construction of pTR-IRBP-RPGRsyn, the plasmid is tested for stability in bacteria using the methods described in Example 1.

Once the stability of pTR-IRBP-RPGRsyn is confirmed, an HSV recombination plasmid comprising the IRBP-RPGRsyn expression cassette (pHSV106-IRBP-RPGRsyn) is constructed. pHSV106-IRBP-RPGRsyn is used for construction of HSV-IRBP-RPGRsyn helper vector for large scale production of the AAV vector AAV-IRBP-RPGRsyn. The rHSV helper viruses are propagated in mammalian cells (V27, an ICP27-complementing Vero cell line). RPGRsyn cDNA is more stable in mammalian cells than in bacteria. This increased stability will eliminate the need for large-scale production of an AAV proviral plasmid containing the RPGRsyn cDNA, which is a reagent required for rAAV production by plasmid transfection methods.

The invention claimed is:

1. An isolated polynucleotide comprising the nucleic acid sequence of SEQ ID NO: 1 encoding a human retinitis pigmentosa GTPase regulator (RPGR) protein.

2. An isolated expression cassette comprising the polynucleotide of claim 1 and an expression control sequence operably linked and heterologous to the nucleic acid sequence.

3. An isolated vector comprising the polynucleotide of claim 1.

4. The vector of claim 3, wherein the vector is a recombinant adeno-associated (rAAV) expression vector.

5. A recombinant herpes simplex virus (rHSV) comprising the polynucleotide of claim 1.

6. An isolated host cell comprising the polynucleotide of claim 1.

7. The host cell of claim 6, wherein the host cell is a mammalian cell.

8. The host cell of claim 6, wherein the host cell is a HeLa cell, a BHK21 cell or a Vero cell.

9. The expression cassette of claim 2, wherein the expression control sequence is a human interphotoreceptor retinoid-binding protein (IRBP) promoter.

10. The expression cassette of claim 9, wherein the human IRBP promoter comprises a nucleic acid sequence having at least 95% sequence identity to the nucleic acid sequence of SEQ ID NO: 8 and directs preferential expression in rods and cones.

11. The expression cassette of claim 9, wherein the human IRBP promoter comprises the nucleic acid sequence of SEQ ID NO: 8.

12. The polynucleotide of claim 1, wherein the polynucleotide comprises the nucleic acid sequence of SEQ ID NO: 7.

13. A method of producing the rAAV expression vector of claim 4, comprising
 (a) infecting a host cell with a recombinant herpes simplex virus (rHSV) comprising the nucleic acid sequence of SEQ ID NO: 1;
 (b) incubating the host cell; and
 (c) following incubation, collecting rAAV from the host cell of step (b).

14. The method of claim 13, wherein the host cell is a HeLa cell, a BHK21 cell or a Vero cell.

15. The method of claim 13, wherein the rHSV further comprises a human IRBP promoter operably linked to the nucleic acid sequence of SEQ ID NO: 1.

16. The method of claim 15, wherein the human IRBP promoter comprises a nucleic acid sequence having at least 95% sequence identity to the nucleic acid sequence of SEQ ID NO: 8 and directs preferential expression in rods and cones.

17. The method of claim 15, wherein the human IRBP promoter comprises the nucleic acid sequence of SEQ ID NO: 8.

18. The method of claim 13, wherein the rHSV comprises the nucleic acid sequence of SEQ ID NO: 7.

* * * * *

SEQUENCE LISTING

<160> NUMBER OF SEQ ID NOS: 12

<210> SEQ ID NO 1
<211> LENGTH: 3459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| atgagagagc | cagaggagct | gatgccagat | agcggagcag | tgtttacctt | cggaaagtcc | 60 |
| aagttcgcag | agaataaccc | aggaaagttc | tggtttaaaa | acgacgtgcc | cgtccacctg | 120 |
| tcttgtggcg | atgagcatag | tgccgtggtc | actgggaaca | ataagctgta | tatgttcggg | 180 |
| tccaacaatt | ggggacagct | ggggctggga | tccaaatctg | ctatctctaa | gccaacctgc | 240 |
| gtgaaggcac | tgaaacccga | gaaggtcaaa | ctggccgctt | gtggcagaaa | ccacactctg | 300 |
| gtgagcaccg | agggcgggaa | tgtctatgcc | accgaggca | acaatgaggg | acagctggga | 360 |
| ctggggggaca | ctgaggaaag | gaataccttt | cacgtgatct | ccttctttac | atctgagcat | 420 |
| aagatcaagc | agctgagcgc | cggctccaac | acatctgcag | ccctgactga | ggacgggcgc | 480 |
| ctgttcatgt | ggggagataa | ttcagagggc | cagattgggc | tgaaaaacgt | gagcaacgtg | 540 |
| tgcgtgcctc | agcaggtgac | catcggaaag | ccagtcagtt | ggatttcatg | tggctactat | 600 |
| catagcgcct | tcgtgaccac | agatggcgag | ctgtacgtct | tggggagcc | cgaaaacgga | 660 |
| aaactgggcc | tgcctaacca | gctgctgggc | aataccgga | caccccagct | ggtgtccgag | 720 |
| atccctgaaa | aagtgatcca | ggtcgcctgc | ggggagagc | atacagtggt | cctgactgag | 780 |
| aatgccgtgt | acaccttcgg | actgggccag | tttggccagc | tggggctggg | aaccttcctg | 840 |
| tttgagacat | ccgaaccaaa | agtgatcgag | aacattcgcg | accagactat | cagctacatt | 900 |
| tcctgcggag | agaatcacac | cgcactgatc | acagacattg | gcctgatgta | acctttggc | 960 |
| gatgggcggc | acgggaagct | gggactgggc | ctggagaact | tcactaatca | cttcatcccc | 1020 |
| accctgtgct | ctaacttcct | gcggttcatc | gtgaaactgg | tcgcttgcgg | cgggtgtcac | 1080 |
| atggtggtct | tcgctgcacc | tcataggggc | gtggctaagg | agatcgaatt | tgacgagatt | 1140 |
| aacgatacat | gcctgagcgt | ggcaactttc | ctgccataca | gctccctgac | ttctggcaat | 1200 |
| gtgctgcaga | gaaccctgag | tgcaaggatg | cggagaaggg | agagggaacg | ctctcctgac | 1260 |
| agtttctcaa | tgcgacgaac | cctgccacct | atcgagggga | cactgggact | gagtgcctgc | 1320 |
| ttcctgccta | actcagtgtt | tccacgatgt | agcgagcgga | atctgcagga | gtctgtcctg | 1380 |
| agtgagcagg | atctgatgca | gccagaggaa | cccgactacc | tgctggatga | gatgaccaag | 1440 |
| gaggccgaaa | tcgacaactc | tagtacagtg | gagtccctgg | gcgagactac | cgatatcctg | 1500 |
| aatatgacac | acattatgtc | actgaacagc | aatgagaaga | gtctgaaact | gtcaccagtg | 1560 |
| cagaagcaga | gaaacagca | gactattggc | gagctgactc | aggacaccgc | cctgacagag | 1620 |
| aacgacgata | gcgatgagta | tgaggaaatg | tccgagatga | aggaaggcaa | agcttgtaag | 1680 |
| cagcatgtga | gtcaggggat | cttcatgaca | cagccagcca | caactattga | ggcttttttca | 1740 |
| gacgaggaag | tggagatccc | cgaggaaaaa | gagggcgcag | aagattccaa | ggggaatgga | 1800 |
| attgaggaac | aggaggtgga | agccaacgag | gaaaatgtga | agtccacgg | aggcaggaag | 1860 |
| gagaaaacag | aaatcctgtc | tgacgatctg | actgacaagg | ccgaggtgtc | cgaaggcaag | 1920 |
| gcaaaatctg | tcggagaggc | agaagacgga | ccagagggac | gaggggatgg | aacctgcgag | 1980 |

```
gaaggctcaa gcggggctga gcattggcag gacgaggaac gagagaaggg cgaaaaggat    2040
aaaggccgcg gggagatgga acgacctgga gagggcgaaa aagagctggc agagaaggag    2100
gaatggaaga aaagggacgg cgaggaacag gagcagaaag aaagggagca gggccaccag    2160
aaggagcgca accaggagat ggaagagggc ggcgaggaag agcatggcga gggagaagag    2220
gaagagggcg atagagaaga ggaagaggaa aaagaaggcg aagggaagga ggaaggagag    2280
ggcgaggaag tggaaggcga gagggaaaag gaggaaggag aacggaagaa agaggaaaga    2340
gccggcaaag aggaaaaggg cgaggaagag ggcgatcagg gcgaaggcga ggaggaagag    2400
accgagggcc gcggggaaga gaaagaggag ggaggagagg tggagggcgg agaggtcgaa    2460
gagggaaagg gcgagcgcga agaggaagag gaagagggcg agggcgagga agaagagggc    2520 gaggggggaag aagagagggg agagggcgaa gaggaagagg gggagggaaa gggcgaagag    2580
gaaggagagg aagggggaggg agaggaagag ggggaggagg gcgaggggga aggcgaggag    2640
gaagaaggag agggggaagg cgaagaggaa ggcgaggggg aaggagagga ggaagaaggg    2700
gaaggcgaag gcgaagagga gggagaagga gaggggaggg aagaggaagg agaagggaag    2760
ggcgaggagg aaggcgaaga gggagagggg gaaggcgagg aagaggaagg cgagggcgaa    2820
ggagaggacg gcgagggcga gggagaagag gaggaagggg aatgggaagg cgaagaagag    2880
gaaggcgaag gcgaaggcga agagaagggc gaagggagg gcgaggaggg cgaaggcgaa    2940
ggggaggaag aggaaggcga agagaaggc gaggaagaag agggagagga ggaaggcgag    3000
gaggaaggag aggggaggga ggagggagaa ggcgagggcg aagaagaaga gagggagaa    3060 gtggagggcg aagtcgaggg ggaggaggga aaggggaag gggaggaaga agagggcgaa    3120
gaagaaggcg aggaaagaga aaagagggga aaggcgagg aaaaccggag aaatagggaa    3180
gaggaggaag aggaagaggg aaagtaccag gagacaggcg aagaggaaaa cgagcggcag    3240
gatggcgagg aatataagaa agtgagcaag atcaaaggat ccgtcaagta cggcaagcac    3300
aaaacctatc agaagaaaag cgtgaccaac acacagggga atggaaaaga gcagcgaagt    3360
aaaatgcctg tgcagtcaaa acggctgctg aagaatggcc caagcgggtc taaaaaattc    3420
tggaacaatg tcctgccaca ctatctggaa ctgaagtaa                          3459
```

<210> SEQ ID NO 2
<211> LENGTH: 2818
<212> TYPE: DNA
<213> ORGANISM: Homo sapiens

<400> SEQUENCE: 2

```
gctccttcct gtactgccca gctccgcttg ctccctgacc atccctgcag cagccctgat     60
gtgtcattgt cccctctta acctgcgctg cagtgctgca gggctgggct ctggagctgg    120
gtctggtcat ttctccttag atatgtagag gcccaggaaa ggtttggagc ctaagaagcc    180
ctaggactcc aggtctccag ggcagcccca gcctcttgga atgactttcc ctaataccac    240
aggggtgttc taatcccagg cagacccaag ctgcccctca ccaactccta cgtcctcaac    300 ttccttcat aacttctagg atggaaacac ctaatcctcc agcaatactg aggctttcct    360
ccttattctg ttttcccttt tgaagaagcc aaggctcaga gcagtcgagt cacctaatca    420
tggtctcatg tcgcctgatc aaggtctcat gtcaccttat caagatctca cccactcacc    480
tattcagttc tcaccagttc agttcaggat ggcttctaag ctaccctgca cagctctgcc    540
cacaggacat ttgtataagt gaggggtgc aggccttcca gccccctcca actccaaaac    600
tcagccccca agatcaagtg gactctctga acccacccctg gccctacagt tgtcagggtc    660
```

```
tggatgggaa gatgtagagc tctcggcttt cactctgggg acttacccag aacatattct    720
cctcatgagc taaggaggct ggctgccatc ttcctacatc cccccacggc ctgggggcaa    780
ggacaccctg gccccctgga gtctggagaa ctctgaggac agaacttgct cttccacctg    840
cttgggcctt acccacagga gaagcactgc ttctctaccc atgccccatc caactcaggc    900
accccaggga cttgcaacag tctgattttt tctcacgtcc ttcttaaggc tctgggctag    960
ccacacaaat caaatcccag tgataggtcc agacaatcct atcctgaaac tacatcttag   1020
taagactcca gggaatcctt tccccaaaga cagtcttact cctgttctcc ccccaagcct   1080
ttctgggcca gaagctttgc ctggactcaa gcaatgcag acaagtgccc tctgaggaca    1140
cggaagtgca tgctcagaac tgtgattctc caagtggagg cagaggagaa ggcccaggct   1200
tcccagcagg gctaaggata tgcaaggagt gcattcatcc ggaggtgttg gcagcatccc   1260
agccccaccc cattctcatc gtaaatcagg ctcacttcca ttggctgcat acggtggagt   1320
gatgtgacca tatgtcactt gagcattaca caaatcctaa tgagctaaaa atatgtttgt   1380
tttagctaat tgacctcttt ggccttcata aagcagttgg taaacatcct cagataatga   1440
tttccaaaga gcagattgtg ggtctcagct gtgcagagaa agcccacgtc ctgagacca    1500 ccttctccag ctgcctactg aggcacacag gggcgcctgc ctgctgcccg ctcagccaag   1560
gcggtgttgc tggagccagc ttgggacagc tctcccaacg ctctgccctg ccttgcgac    1620 cactctctgg gccgtagttg tctgtctgtt aagtgaggaa agtgcccatc tccagaggca   1680
ttcagcggca aagcagggct tccaggttcc gaccccatag caggacttct tggatttcta   1740
cagccagtca gttgcaagca gcacccatat tatttctata agaagtggca ggagctggga   1800
tctgaagagt tcagcagtct acctttccct gtttcttgtg ctttatgcag tcaggaggaa   1860
tgatctggat tccatgtgaa gcctgggacc acggagaccc aagacttcct gcttgattct   1920
ccctgcgaac tgcaggctgt gggctgagcc ttcaagaagc aggagtcccc tctagccatt   1980
aactctcaga gctaacctca tttgaatggg aacactagtc ctgtgatgtc tggaaggtgg   2040
gcgcctctac actccacacc ctacatggtg gtccagacac atcattccca gcattagaaa   2100
gctgtagggg gacccgttct gttccctgga ggcattaaag ggacatagaa ataaatctca   2160
agctctgagg ctgatgccag cctcagactc agcctctgca ctgtatgggc caattgtagc   2220
cccaaggact tcttcttgct gcaccccta tctgtccaca cctaaaacga tgggcttcta    2280
tttagttaca gaactctctg gcctgtttg ttttgctttg ctttgttttg ttttgttttt    2340 ttgtttttt gttttttagc tatgaaacag aggtaatatc taatacagat aacttaccag    2400
taatgagtgc ttcctactta ctgggtactg ggaagaagtg ctttacacat attttctcat    2460
ttaatctaca caataagtaa ttaagacatt tccctgaggc cacgggagag acagtggcag   2520
aacagttctc caaggaggac ttgcaagtta ataactggac tttgcaaggc tctggtggaa   2580
actgtcagct tgtaaaggat ggagcacagt gtctggcatg tagcaggaac taaaataatg   2640
gcagtgatta atgttatgat atgcagacac aacacagcaa gataagatgc aatgtacctt   2700
ctgggtcaaa ccaccctggc cactcctccc cgatacccag ggttgatgtg cttgaattag   2760
acaggattaa aggcttactg gagctggaag ccttgcccca actcaggagt ttagcccc    2818
```

<210> SEQ ID NO 3
<211> LENGTH: 1326
<212> TYPE: DNA
<213> ORGANISM: Homo sapiens

<400> SEQUENCE: 3

```
ctgcctactg aggcacacag gggcgcctgc ctgctgcccg ctcagccaag gcggtgttgc      60
tggagccagc ttgggacagc tctcccaacg ctctgccctg gccttgcgac cactctctgg     120
gccgtagttg tctgtctgtt aagtgaggaa agtgcccatc tccagaggca ttcagcggca     180
aagcagggct tccaggttcc gaccccatag caggacttct tggatttcta cagccagtca     240
gttgcaagca gcacccatat tatttctata agaagtggca ggagctggga tctgaagagt     300
tcagcagtct acctttccct gtttcttgtg ctttatgcag tcaggaggaa tgatctggat     360
tccatgtgaa gcctgggacc acggagaccc aagacttcct gcttgattct ccctgcgaac     420
tgcaggctgt gggctgagcc ttcaagaagc aggagtcccc tctagccatt aactctcaga     480
gctaacctca tttgaatggg aacactagtc ctgtgatgtc tggaaggtgg gcgcctctac     540
actccacacc ctacatggtg gtccagacac atcattccca gcattagaaa gctgtagggg     600
gacccgttct gttccctgga ggcattaaag ggacatagaa ataaatctca agctctgagg     660
ctgatgccag cctcagactc agcctctgca ctgtatgggc caattgtagc cccaaggact     720
tcttcttgct gcaccccta tctgtccaca cctaaaacga tgggcttcta tttagttaca     780
gaactctctg gcctgttttg ttttgctttg ctttgttttg ttttgttttt ttgttttttt     840
gtttttagc tatgaaacag aggtaatatc taatacagat aacttaccag taatgagtgc     900
ttcctactta ctgggtactg ggaagaagtg ctttacacat attttctcat ttaatctaca     960
caataagtaa ttaagacatt tccctgaggc cacgggagag acagtggcag aacagttctc    1020
caaggaggac ttgcaagtta ataactggac tttgcaaggc tctggtggaa actgtcagct    1080
tgtaaaggat ggagcacagt gtctggcatg tagcaggaac taaaataatg gcagtgatta    1140
atgttatgat atgcagacac aacacagcaa gataagatgc aatgtacctt ctgggtcaaa    1200
ccaccctggc cactcctccc cgataccccag ggttgatgtg cttgaattag acaggattaa    1260
aggcttactg gagctggaag ccttgcccca actcaggagt ttagccccag accttctgtc    1320
caccag                                                                1326
```

<210> SEQ ID NO 4
<211> LENGTH: 70
<212> TYPE: DNA
<213> ORGANISM: Mus musculus

<400> SEQUENCE: 4

```
gcttgaatta gacaggatta aaggcttact ggagctggaa gccttgcccc aactcaggag      60
tttagcccca                                                             70
```

<210> SEQ ID NO 5
<211> LENGTH: 3459
<212> TYPE: DNA
<213> ORGANISM: Homo sapiens

<400> SEQUENCE: 5

```
atgagggagc cggaagagct gatgcccgat tcgggtgctg tgtttacatt tgggaaaagt      60
aaatttgctg aaaataatcc cggtaaattc tggttaaaa atgatgtccc tgtacatctt     120
tcatgtggag atgaacattc tgctgttgtt accggaaata taaactttta catgtttggc     180
agtaacaact ggggtcagtt aggattagga tcaaagtcag ccatcagcaa gccaacatgt     240
gtcaaagctc taaaacctga aaagtgaaa ttagctgcct gtggaaggaa ccacaccctg     300
gtgtcaacag aaggaggcaa tgtatatgca actggtggaa ataatgaagg acagttgggg    360
```

```
cttggtgaca ccgaagaaag aaacactttt catgtaatta gcttttttac atccgagcat      420
aagattaagc agctgtctgc tggatctaat acttcagctg ccctaactga ggatggaaga      480 cttttatgt ggggtgacaa ttccgaaggg caaattggtt taaaaaatgt aagtaatgtc       540
tgtgtccctc agcaagtgac cattgggaaa cctgtctcct ggatctcttg tggatattac      600
cattcagctt ttgtaacaac agatggtgag ctatatgtgt ttggagaacc tgagaatggg      660
aagttaggtc ttcccaatca gctcctgggc aatcacagaa caccccagct ggtgtctgaa      720
attccggaga aggtgatcca agtagcctgt ggtggagagc atactgtggt tctcacggag      780
aatgctgtgt atacctttgg gctgggacaa tttggtcagc tgggtcttgg cacttttctt      840
tttgaaactt cagaacccaa agtcattgag aatattaggg atcaaacaat aagttatatt      900
tcttgtggag aaaatcacac agctttgata acagatatcg gccttatgta tacttttgga      960
gatggtcgcc acggaaaatt aggacttgga ctggagaatt ttaccaatca cttcattcct     1020
actttgtgct ctaattttt gaggtttata gttaaattgg ttgcttgtgg tggatgtcac      1080
atggtagttt ttgctgctcc tcatcgtggt gtggcaaaag aaattgaatt cgatgaaata     1140
aatgatactt gcttatctgt ggcgactttt ctgccgtata gcagtttaac ctcaggaaat     1200
gtactgcaga ggactctatc agcacgtatg cggcgaagag agagggagag gtctccagat     1260 tcttttcaa tgaggagaac actacctcca atagaaggga ctcttggcct ttctgcttgt      1320
tttctcccca attcagtctt tccacgatgt tctgagagaa acctccaaga gagtgtctta     1380
tctgaacagg acctcatgca gccagaggaa ccagattatt tgctagatga aatgaccaaa     1440
gaagcagaga tagataattc ttcaactgta gaaagccttg gagaaactac tgatatctta     1500
aacatgacac acatcatgag cctgaattcc aatgaaaagt cattaaaatt atcaccagtt     1560
cagaaacaaa agaaacaaca aacaattggg gaactgacgc aggatacagc tcttactgaa     1620
aacgatgata gtgatgaata tgaagaaatg tcagaaatga agaagggaa agcatgtaaa      1680 caacatgtgt cacaagggat tttcatgacg cagccagcta cgactatcga agcattttca     1740
gatgaggaag tagagatccc agaggagaag gaaggagcag aggattcaaa aggaaatgga     1800
atagaggagc aagaggtaga agcaaatgag gaaaatgtga aggtgcatgg aggaagaaag     1860
gagaaaacag agatcctatc agatgacctt acagacaaag cagaggtgag tgaaggcaag     1920
gcaaaatcag tgggagaagc agaggatggg cctgaaggta gagggatgg aacctgtgag      1980 gaaggtagtt caggagcaga acactggcaa gatgaggaga gggagaaggg ggagaaagac     2040
aagggtagag agaaatggag gaggccagga gaggagaga aggaactagc agagaaggaa      2100
gaatggaaga gagggatgg ggaagagcag gagcaaaagg agagggagca gggccatcag      2160
aaggaaagaa accaagagat ggaggaggga gggaggagg agcatggaga aggagaagaa      2220
gaggagggag acagagaaga ggaagaagag aaggagggag aagggaaaga ggaaggagaa     2280
ggggaagaag tggagggaga acgtgaaaag gaggaaggag agaggaaaaa ggaggaaaga     2340
gcggggaagg aggagaaagg agaggaagaa ggagaccaag gagaggggga agaggaggaa     2400
acagagggga gagggaggga aaaagaggag ggaggggaag tagagggagg ggaagtagag     2460
gaggggaaag gagagaggga agaggaagag gaggagggtg aggggaaga ggaggaaggg      2520 gaggggaag aggaggaagg gaggggaa gaggaggaag gagaagggaa aggaggaa         2580 gaaggggaag aaggagaagg gggaggaagaa ggggaggaag gagaagggga ggggaagag     2640 gaggaaggag aaggggaggg agaagaggaa ggagaagggaa agggagaaga ggaggaagga    2700
```

```
gaagggagg gagaagagga aggagaaggg gagggagaag aggaggaagg agaagggaaa      2760
ggggaggagg aaggagagga aggagaaggg gaggggggaag aggaggaagg agaagggaa     2820 ggggaggatg gagaaggga ggggggaagag gaggaaggag aatgggaggg ggaagaggag     2880
gaaggagaag gggagggga agaggaagga gaagggggaag gggaggaagg agaaggggag    2940
ggggaagagg aggaaggaga aggggagggg gaagaggagg aagggggaaga agaaggggag    3000 gaagaaggag agggagagga agaaggggag ggagaagggg aggaagaaga ggaaggggaa     3060
gtggaagggg aggtggaagg ggaggaagga gaggggggaag gagaggaaga ggaaggagag    3120
gaggaaggag aagaagggga aaaggagggg gaaggagaag aaaacaggag gaacagagaa     3180
gaggaggagg aagaagaggg gaagtatcag gagacaggcg aagaagagaa tgaaaggcag     3240
gatggagagg agtacaaaaa agtgagcaaa ataaaaggat ctgtgaaata tggcaaacat     3300
aaaacatatc aaaaaaagtc agttactaac acacaggaa atgggaaaga gcagaggtcc      3360
aaaatgccag tccagtcaaa acgactttta aaaaacgggc catcaggttc caaaaagttc    3420
tggaataatg tattaccaca ttacttggaa ttgaagtaa                           3459
```

<210> SEQ ID NO 6
<211> LENGTH: 1152
<212> TYPE: PRT
<213> ORGANISM: Homo sapiens

<400> SEQUENCE: 6

```
Met Arg Glu Pro Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
                35                  40                  45

Val Val Thr Gly Asn Asn Lys Leu Tyr Met Phe Gly Ser Asn Asn Trp
            50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
                100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
        130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
                180                 185                 190

Ser Trp Ile Ser Cys Gly Tyr Tyr His Ser Ala Phe Val Thr Thr Asp
            195                 200                 205

Gly Glu Leu Tyr Val Phe Gly Glu Pro Glu Asn Gly Lys Leu Gly Leu
        210                 215                 220

Pro Asn Gln Leu Leu Gly Asn His Arg Thr Pro Gln Leu Val Ser Glu
225                 230                 235                 240
```

-continued

Ile Pro Glu Lys Val Ile Gln Val Ala Cys Gly Gly Glu His Thr Val
            245                 250                 255

Val Leu Thr Glu Asn Ala Val Tyr Thr Phe Gly Leu Gly Gln Phe Gly
        260                 265                 270

Gln Leu Gly Leu Gly Thr Phe Leu Phe Glu Thr Ser Glu Pro Lys Val
        275                 280                 285

Ile Glu Asn Ile Arg Asp Gln Thr Ile Ser Tyr Ile Ser Cys Gly Glu
        290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
                340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
        370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
                420                 425                 430

Gly Thr Leu Gly Leu Ser Ala Cys Phe Leu Pro Asn Ser Val Phe Pro
        435                 440                 445

Arg Cys Ser Glu Arg Asn Leu Gln Glu Ser Val Leu Ser Gln Asp
450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
        515                 520                 525

Ile Gly Glu Leu Thr Gln Asp Thr Ala Leu Thr Glu Asn Asp Asp Ser
        530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
            580                 585                 590

Ala Glu Asp Ser Lys Gly Asn Gly Ile Glu Glu Gln Glu Val Glu Ala
        595                 600                 605

Asn Glu Glu Asn Val Lys Val His Gly Gly Arg Lys Glu Lys Thr Glu
    610                 615                 620

Ile Leu Ser Asp Asp Leu Thr Asp Lys Ala Glu Val Ser Glu Gly Lys
625                 630                 635                 640

Ala Lys Ser Val Gly Glu Ala Glu Asp Gly Pro Glu Gly Arg Gly Asp
                645                 650                 655

Gly Thr Cys Glu Glu Gly Ser Ser Gly Ala Glu His Trp Gln Asp Glu

-continued

```
            660                 665                 670
Glu Arg Glu Lys Gly Glu Lys Asp Lys Gly Arg Gly Glu Met Glu Arg
        675                 680                 685
Pro Gly Glu Gly Glu Lys Glu Leu Ala Glu Lys Glu Glu Trp Lys Lys
        690                 695                 700
Arg Asp Gly Glu Glu Gln Gln Lys Glu Arg Glu Gln Gly His Gln
705                 710                 715                 720
Lys Glu Arg Asn Gln Glu Met Glu Glu Gly Glu Glu His Gly
            725                 730                 735
Glu Gly Glu Glu Glu Gly Asp Arg Glu Glu Glu Glu Lys Glu
            740                 745                 750
Gly Glu Gly Lys Glu Glu Glu Glu Val Glu Gly Glu Arg
        755                 760                 765
Glu Lys Glu Glu Gly Glu Arg Lys Lys Glu Glu Arg Ala Gly Lys Glu
        770                 775                 780
Glu Lys Gly Glu Glu Gly Asp Gln Gly Glu Gly Glu Glu Glu
785                 790                 795                 800
Thr Glu Gly Arg Gly Glu Glu Lys Glu Glu Gly Glu Val Glu Gly
            805                 810                 815
Gly Glu Val Glu Glu Gly Lys Gly Glu Arg Glu Glu Glu Glu
        820                 825                 830
Gly Glu Gly Glu Gly Glu Gly Glu Gly Glu Glu Glu Gly Glu
        835                 840                 845
Gly Glu Glu Glu Gly Glu Gly Lys Gly Glu Glu Gly Glu Glu
850                 855                 860
Gly Glu Gly Glu Gly Glu Gly Glu Gly Glu Gly Glu Gly Glu
865                 870                 875                 880
Glu Glu Gly Glu Gly Glu Gly Glu Glu Gly Glu Gly Glu Gly Glu
            885                 890                 895
Glu Glu Glu Gly Glu Gly Glu Gly Glu Glu Gly Glu Gly Glu Gly
            900                 905                 910
Glu Glu Glu Glu Gly Glu Gly Lys Gly Glu Glu Glu Gly Glu Glu Gly
        915                 920                 925
Glu Gly Glu Gly Glu Glu Glu Gly Glu Gly Glu Gly Glu Asp Gly
        930                 935                 940
Glu Gly Glu Gly Glu Glu Glu Gly Glu Trp Glu Gly Glu Glu
945                 950                 955                 960
Glu Gly Glu Gly Glu Gly Glu Glu Glu Gly Glu Gly Glu Gly Glu
            965                 970                 975
Gly Glu Gly Glu Gly Glu Glu Glu Gly Glu Gly Glu Gly Glu Glu
            980                 985                 990
Glu Glu Gly Glu Gly Glu Gly Glu  Glu Glu Gly Glu Gly  Glu Glu Glu
            995                 1000                1005
Gly Glu  Gly Glu Gly Glu Glu  Glu Glu Glu Gly Glu  Val Glu Gly
        1010                1015                1020
Glu Val  Glu Gly Glu Glu Gly  Glu Gly Glu Gly Glu  Glu Glu Glu
        1025                1030                1035
Gly Glu  Glu Glu Gly Glu Glu  Arg Glu Lys Glu Gly  Glu Gly Glu
        1040                1045                1050
Glu Asn  Arg Arg Asn Arg Glu  Glu Glu Glu Glu  Glu Gly Lys
        1055                1060                1065
Tyr Gln  Glu Thr Gly Glu Glu  Glu Asn Glu Arg Gln  Asp Gly Glu
        1070                1075                1080
```

| Glu | Tyr | Lys | Lys | Val | Ser | Lys | Ile | Lys | Gly | Ser | Val | Lys | Tyr | Gly |
| 1085 | | | | | 1090 | | | | | 1095 | | | | |
| Lys | His | Lys | Thr | Tyr | Gln | Lys | Lys | Ser | Val | Thr | Asn | Thr | Gln | Gly |
| 1100 | | | | | 1105 | | | | | 1110 | | | | |
| Asn | Gly | Lys | Glu | Gln | Arg | Ser | Lys | Met | Pro | Val | Gln | Ser | Lys | Arg |
| 1115 | | | | | 1120 | | | | | 1125 | | | | |
| Leu | Leu | Lys | Asn | Gly | Pro | Ser | Gly | Ser | Lys | Lys | Phe | Trp | Asn | Asn |
| 1130 | | | | | 1135 | | | | | 1140 | | | | |
| Val | Leu | Pro | His | Tyr | Leu | Glu | Leu | Lys | | | | | | |
| 1145 | | | | | 1150 | | | | | | | | | |

<210> SEQ ID NO 7
<211> LENGTH: 3871
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
tctagactcg aggaactgaa aaaccagaaa gttaactggt aagtttagtc tttttgtctt      60
ttatttcagg tcccggatcc ggtggtggtg caaatcaaag aactgctcct cagtggatgt     120
tgcctttact ctaggcctg tacggaagtg ttacttctgc tctaaaagct gcggaattgt      180
acccgcggcc gcgccaccat gagagagcca gaggagctga tgccagatag cggagcagtg     240
tttaccttcg gaaagtccaa gttcgcgag aataacccag gaaagttctg gtttaaaaac     300
gacgtgcccg tccacctgtc ttgtggcgat gagcatagtg ccgtggtcac tgggaacaat    360
aagctgtata tgttcgggtc caacaattgg ggacagctgg ggctgggatc caaatctgct    420
atctctaagc aacctgcgt gaaggcactg aaacccgaga aggtcaaact ggccgcttgt    480
ggcagaaacc acactctggt gagcaccgag ggcgggaatg tctatgccac cggaggcaac    540
aatgagggac agctgggact ggggacact gaggaaagga ataccttca cgtgatctcc    600
ttctttacat ctgagcataa gatcaagcag ctgagcgccg gctccaacac atctgcagcc    660
ctgactgagg acgggcgcct gttcatgtgg ggagataatt cagagggcca gattgggctg    720
aaaaacgtga gcaacgtgtg cgtgcctcag caggtgacca tcggaaagcc agtcagttgg    780
atttcatgtg gctactatca tagcgccttc gtgaccacag atggcgagct gtacgtcttt    840
ggggagcccg aaaacggaaa actgggcctg cctaaccagc tgctgggcaa tcaccggaca    900
ccccagctgg tgtccgagat ccctgaaaaa gtgatccagg tcgcctgcgg gggagagcat    960
acagtggtcc tgactgagaa tgccgtgtac accttcggac tgggccagtt tggccagctg   1020
gggctgggaa ccttcctgtt tgagacatcc gaaccaaaag tgatcgagaa cattcgcgac   1080
cagactatca gctacatttc tgcggagag aatcacaccg cactgatcac agacattggc   1140
ctgatgtata ccttttggcga tgggcggcac gggaagctgg gactgggcct ggagaacttc   1200
actaatcact tcatccccac cctgtgctct aacttcctgc ggttcatcgt gaaactggtc   1260
gcttgcggcg gtgtcacat ggtggtcttc gctgcacctc ataggggcgt ggctaaggag   1320
atcgaatttg acgagattaa cgatacatgc ctgagcgtgg caactttcct gccatacagc   1380
tccctgactt ctggcaatgt gctgcagaga accctgagtg caaggatgcg gagaagggag   1440
agggaacgct ctcctgacag tttctcaatg cgacgaaccc tgccacctat cgaggggaca   1500
ctgggactga gtgcctgctt cctgcctaac tcagtgtttc cacgatgtag cgagcggaat   1560
```

```
ctgcaggagt ctgtcctgag tgagcaggat ctgatgcagc cagaggaacc cgactacctg     1620
ctggatgaga tgaccaagga ggccgaaatc gacaactcta gtacagtgga gtccctgggc     1680
gagactaccg atatcctgaa tatgacacac attatgtcac tgaacagcaa tgagaagagt     1740
ctgaaactgt caccagtgca gaagcagaag aaacagcaga ctattggcga gctgactcag     1800
gacaccgccc tgacagagaa cgacgatagc gatgagtatg aggaaatgtc cgagatgaag     1860
gaaggcaaag cttgtaagca gcatgtgagt caggggatct tcatgacaca gccagccaca     1920
actattgagg ctttttcaga cgaggaagtg gagatccccg aggaaaaaga gggcgcagaa     1980
gattccaagg ggaatggaat tgaggaacag gaggtggaag ccaacgagga aaatgtgaaa     2040
gtccacggag gcaggaagga gaaaacagaa atcctgtctg acgatctgac tgacaaggcc     2100
gaggtgtccg aaggcaaggc aaaatctgtc ggagaggcag aagacggacc agagggacga     2160
ggggatggaa cctgcgagga aggctcaagc ggggctgagc attggcagga cgaggaacga     2220
gagaagggcg aaaaggataa aggccgcggg gagatggaac gacctggaga gggcgaaaaa     2280
gagctggcag agaaggagga atggaagaaa agggacggcg aggaacagga gcagaaagaa     2340
agggagcagg gccaccagaa ggagcgcaac caggagatgg aagagggcgg cgaggaagag     2400
catggcgagg agaagagga agagggcgat agagaagagg aagaggaaaa agaaggcgaa     2460
gggaaggagg aaggagaggg cgaggaagtg gaaggcgaga gggaaaagga ggaaggagaa     2520
cggaagaaag aggaaagagc cggcaaagag gaaaagggcg aggaagaggg cgatcagggc     2580
gaaggcgagg aggaagagac cgagggccgc ggggaagaga agaggagggg aggagaggtg     2640
gagggcggag aggtcgaaga gggaaagggc gagcgcgaag aggaagagga agagggcgag     2700
ggcgaggaag aagagggcga gggggaagaa gaggagggag agggcgaaga ggaagagggg     2760
gagggaaagg gcgaagagga aggagaggaa ggggagggag aggaagaggg ggaggagggc     2820 gaggggaag gcgaggagga agaaggagag ggggaaggcg aagaggaagg cgaggggaa     2880 ggagaggagg aagaagggga aggcgaaggc gaagaggagg gagaaggaga ggggaggaa     2940 gaggaaggag aagggaaggg cgaggaggaa ggcgaagagg gagagggga aggcgaggaa     3000 gaggaaggcg agggcgaagg agaggacggc gagggcgagg gagaagagga ggaagggaa     3060 tgggaaggcg aagaagagga aggcgaaggc gaaggcgaag aagagggcga aggggagggc     3120
gaggagggcg aaggcgaagg ggaggaagag gaaggcgaag gagaaggcga ggaagaagag     3180
ggagaggagg aaggcgagga ggaaggagag ggggaggagg agggagaagg cgagggcgaa     3240
gaagaagaag agggagaagt ggagggcgaa gtcgaggggg aggagggaga aggggaaggg     3300
gaggaagaag agggcgaaga agaaggcgag gaaagagaaa agagggaga aggcgaggaa     3360 aaccggagaa atagggaaga ggaggaagag gaagagggaa agtaccagga gacaggcgaa     3420
gaggaaaacg agcggcagga tggcgaggaa tataagaaag tgagcaagat caaaggatcc     3480
gtcaagtacg gcaagcacaa aacctatcag aagaaaagcg tgaccaacac acagggggaat     3540 ggaaaagagc agcgaagtaa aatgcctgtg cagtcaaaac ggctgctgaa gaatggccca     3600
agcgggtcta aaaaattctg gaacaatgtc ctgccacact atctggaact gaagtaagcg     3660
gccgcgcgga tccagacatg ataagataca ttgatgagtt tggacaaacc acaactagaa     3720
tgcagtgaaa aaaatgcttt atttgtgaaa tttgtgatgc tattgcttta tttgtaacca     3780
ttataagctg caataaacaa gttaacaaca acaattgcat tcatttatg tttcaggttc     3840 agggggaggt gtgggaggtt ttttagcatg c                                    3871
```

```
<210> SEQ ID NO 8
<211> LENGTH: 235
<212> TYPE: DNA
<213> ORGANISM: Homo sapiens

<400> SEQUENCE: 8
agcacagtgt ctggcatgta gcaggaacta aaataatggc agtgattaat gttatgatat    60
gcagacacaa cacagcaaga taagatgcaa tgtaccttct gggtcaaacc accctggcca   120
ctcctcyccg atacccaggg ttgatgtgct tgaattagac aggattaaag gcttactgga   180
gctggaagcc ttgccccaac tcaggagttt agccccagac cttctgtcca ccagc        235

<210> SEQ ID NO 9
<211> LENGTH: 9
<212> TYPE: PRT
<213> ORGANISM: Homo sapiens

<400> SEQUENCE: 9

Glu Glu Glu Gly Glu Gly Glu Gly Glu
1               5

<210> SEQ ID NO 10
<211> LENGTH: 6
<212> TYPE: PRT
<213> ORGANISM: Mus musculus

<400> SEQUENCE: 10

Glu Glu Gly Glu Gly Glu
1               5

<210> SEQ ID NO 11
<211> LENGTH: 4107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
agatctgaat tcagcacagt gtctggcatg tagcaggaac taaaataatg gcagtgatta    60
atgttatgat atgcagacac aacacagcaa gataagatgc aatgtacctt ctgggtcaaa   120
ccaccctggc cactcctccc cgatacccag ggttgatgtg cttgaattag acaggattaa   180
aggcttactg gagctggaag ccttgcccca actcaggagt ttagccccag accttctgtc   240
caccagctct agactcgagg aactgaaaaa ccagaaagtt aactggtaag tttagtcttt   300
ttgtctttta tttcaggtcc cggatccggt ggtggtgcaa atcaaagaac tgctcctcag   360
tgatgttgc ctttacttct aggcctgtac ggaagtgtta cttctgctct aaaagctgcg   420
gaattgtacc cgcggccgcg ccaccatgag agagccagag agctgatgc cagatagcgg   480
agcagtgttt accttcggaa agtccaagtt cgcagagaat aacccaggaa agttctggtt   540
taaaaacgac gtgcccgtcc acctgtcttg tggcgatgag catagtgccg tggtcactgg   600
gaacaataag ctgtatatgt tcgggtccaa caattgggga cagctggggc tgggatccaa   660
atctgctatc tctaagccaa cctgcgtgaa ggcactgaaa cccgagaagg tcaaactggc   720
cgcttgtggc agaaaccaca ctctggtgag caccgagggc gggaatgtct atgccaccgg   780
aggcaacaat gagggacagc tgggactggg ggacactgag gaaaggaata cctttcacgt   840
gatctccttc tttacatctg agcataagat caagcagctg agcgccggct ccaacacatc   900
tgcagccctg actgaggacg gccgcctgtt catgtgggga gataattcag agggccagat   960
```

```
tgggctgaaa aacgtgagca acgtgtgcgt gcctcagcag gtgaccatcg gaaagccagt    1020
cagttggatt tcatgtggct actatcatag cgccttcgtg accacagatg gcgagctgta    1080
cgtctttggg gagcccgaaa acggaaaact gggcctgcct aaccagctgc tgggcaatca    1140
ccggacaccc cagctggtgt ccgagatccc tgaaaaagtg atccaggtcg cctgcggggg    1200
agagcataca gtggtcctga ctgagaatgc cgtgtacacc ttcggactgg gccagtttgg    1260
ccagctgggg ctgggaacct tcctgtttga cataccgaa ccaaaagtga tcgagaacat    1320
tcgcgaccag actatcagct acatttcctg cggagagaat cacaccgcac tgatcacaga    1380
cattggccta atgtatacct ttggcgatgg gcggcacggg aagctgggac tgggcctgga    1440
gaacttcact aatcacttca tccccaccct gtgctctaac ttcctgcggt tcatcgtgaa    1500
actggtcgct tgcggcgggt gtcacatggt ggtcttcgct gcacctcata ggggcgtggc    1560
taaggagatc gaatttgacg agattaacga tacatgcctg agcgtggcaa ctttcctgcc    1620
atacagctcc ctgacttctg gcaatgtgct gcagagaacc ctgagtgcaa ggatgcggag    1680
aagggagagg gaacgctctc ctgacagttt ctcaatgcga cgaaccctgc cacctatcga    1740
ggggacactg ggactgagtg cctgcttcct gcctaactca gtgtttccac gatgtagcga    1800
gcggaatctg caggagtctg tcctgagtga gcaggatctg atgcagccag aggaacccga    1860
ctacctgctg gatgagatga ccaaggaggc cgaaatcgac aactctagta cagtggagtc    1920
cctgggcgag actaccgata tcctgaatat gacacacatt atgtcactga acagcaatga    1980
gaagagtctg aaactgtcac cagtgcagaa gcagaagaaa cagcagacta ttggcgagct    2040
gactcaggac accgccctga cagagaacga cgatagcgat gagtatgagg aaatgtccga    2100
gatgaaggaa ggcaaagctt gtaagcagca tgtgagtcag gggatcttca tgacacagcc    2160
agccacaact attgaggctt tttcagacga ggaagtggag atccccgagg aaaaagaggg    2220
cgcagaagat tccaagggga atggaattga ggaacaggag gtggaagcca acgaggaaaa    2280
tgtgaaagtc cacggaggca ggaaggagaa aacagaaatc ctgtctgacg atctgactga    2340
caaggccgag gtgtccgaag gcaaggcaaa atctgtcgga gaggcagaag acggaccaga    2400
gggacgaggg gatggaacct gcgaggaagg ctcaagcggg gctgagcatt ggcaggacga    2460
ggaacgagag aagggcgaaa aggataaagg ccgcggggag atggaacgac ctggagaggg    2520
cgaaaaagag ctggcagaga aggaggaatg gaagaaaagg gacggcgagg aacaggagca    2580
gaaagaaagg gagcagggcc accagaagga gcgcaaccag gagatggaag agggcggcga    2640
ggaagagcat ggcgagggag aagaggaaga gggcgataga gaagaggaag aggaaaaaga    2700
aggcgaaggg aaggaggaag gagagggcga ggaagtggaa ggcgagaggg aaaaggagga    2760
aggagaacga agaaagagg aaagagccgg caaagaggaa aagggcgagg aagagggcga    2820
tcagggcgaa ggcgaggagg aagagaccga gggccgcggg gaagagaaag gaggggagg    2880 agaggtggag ggcggagagg tcgaagaggg aaagggcgag cgcgaagagg aagaggaaga    2940
gggcgagggc gaggaagaag agggcgaggg ggaagaagag gagggagagg gcgaagagga    3000 agaggggggag ggaaagggcg aagaggaagg agaggaaggg gagggagagg aagaggggga    3060
ggagggcgag ggggaaggcg aggaggaaga aggagagggg gaaggcgaag aggaaggcga    3120
gggggaagga gaggaggaag aaggggaagg cgaaggcgaa gaggagggag aaggagaggg    3180
ggaggaagag gaaggagaag ggaagggcga ggaggaaggc gaagagggag aggggggaagg    3240 cgaggaagag gaaggcgagg gcgaaggaga ggacggcgag ggcgagggag aagaggagga    3300
```

```
aggggaatgg gaaggcgaag aagaggaagg cgaaggcgaa ggcgaagaag agggcgaagg      3360
ggagggcgag gagggcgaag gcgaaggggga ggaagaggaa ggcgaaggag aaggcgagga     3420
agaagaggga gaggaggaag gcgaggagga aggagagggg gaggaggagg gagaaggcga     3480
gggcgaagaa gaagaagagg gagaagtgga gggcgaagtc gagggggagg agggagaagg     3540
ggaaggggag gaagaagagg gcgaagaaga aggcgaggaa agagaaaaag agggagaagg     3600
cgaggaaaac cggagaaata gggaagagga ggaagaggaa gagggaaagt accaggagac     3660
aggcgaagag gaaaacgagc ggcaggatgg cgaggaatat aagaaagtga gcaagatcaa     3720
aggatccgtc aagtacggca agcacaaaac ctatcagaag aaaagcgtga ccaacacaca     3780
ggggaatgga aaagagcagc gaagtaaaat gcctgtgcag tcaaaacggc tgctgaagaa     3840
tggcccaagc gggtctaaaa aattctggaa caatgtcctg ccacactatc tggaactgaa     3900
gtaagcggcc gcgcggatcc agacatgata agatacattg atgagtttgg acaaaccaca     3960
actagaatgc agtgaaaaaa atgctttatt tgtgaaattt gtgatgctat tgctttattt     4020
gtaaccatta taagctgcaa taaacaagtt aacaacaaca attgcattca ttttatgttt     4080
caggttcagg gggaggtgtg ggaggtt                                         4107

<210> SEQ ID NO 12
<211> LENGTH: 4142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gcagagaggg agtggccaac ctcctagatc tgaattcagc acagtgtctg gcatgtagca       60
ggaactaaaa taatggcagt gattaatgtt atgatatgca gacacaacac agcaagataa      120
gatgcaatgt accttctggg tcaaaccacc ctggccactc ctccccgata cccagggttg      180
atgtgcttga attagacagg attaaaggct tactggagct ggaagccttg ccccaactca      240
ggagtttagc cccagacctt ctgtccacca gctctagact cgaggaactg aaaaaccaga      300
aagttaactg gtaagtttag tcttttttgtc ttttatttca ggtcccggat ccggtggtgg      360
tgcaaatcaa agaactgctc ctcagtggat gttgccttta cttctaggcc tgtacggaag      420
tgttacttct gctctaaaag ctgcggaatt gtacccgcgg ccgcgccacc atgagagagc      480
cagaggagct gatgccagat agcggagcag tgtttacctt cggaaagtcc aagttcgcag      540
agaataaccc aggaaagttc tggtttaaaa acgacgtgcc cgtccacctg tcttgtggcg      600
atgagcatag tgccgtggtc actgggaaca ataagctgta tatgttcggg tccaacaatt      660
ggggacagct ggggctggga tccaaatctg ctatctctaa gccaacctgc gtgaaggcac      720
tgaaacccga gaaggtcaaa ctggccgctt gtggcagaaa ccacactctg gtgagcaccg      780
agggcgggaa tgtctatgcc accgaggca acaatgaggg acagctggga ctggggggaca      840 ctgaggaaag gaataccttt cacgtgatct ccttctttac atctgagcat aagatcaagc      900
agctgagcgc cggctccaac acatctgcag ccctgactga ggacgggcgc ctgttcatgt      960
ggggagataa ttcagagggc cagattgggc tgaaaaacgt gagcaacgtg tgcgtgcctc     1020
agcaggtgac catcggaaag ccagtcagtt ggattcatg tggctactat catagcgcct     1080
tcgtgaccac agatgcgag ctgtacgtct tggggagcc cgaaaacgga aaactgggcc     1140
tgcctaacca gctgctgggc aatcaccgga caccccagct ggtgtccgag atccctgaaa     1200
```

```
aagtgatcca ggtcgcctgc gggggagagc atacagtggt cctgactgag aatgccgtgt    1260
acaccttcgg actgggccag tttggccagc tggggctggg aaccttcctg tttgagacat    1320
ccgaaccaaa agtgatcgag aacattcgcg accagactat cagctacatt tcctgcggag    1380
agaatcacac cgcactgatc acagacattg gcctgatgta tacctttggc gatgggcggc    1440
acgggaagct gggactgggc ctggagaact tcactaatca cttcatcccc accctgtgct    1500
ctaacttcct gcggttcatc gtgaaactgg tcgcttgcgg cgggtgtcac atggtggtct    1560
tcgctgcacc tcatagggc gtggctaagg agatcgaatt tgacgagatt aacgatacat    1620
gcctgagcgt ggcaactttc ctgccataca gctccctgac ttctggcaat gtgctgcaga    1680
gaaccctgag tgcaaggatg cggagaaggg agagggaacg ctctcctgac agtttctcaa    1740
tgcgacgaac cctgccacct atcgagggga cactgggact gagtgcctgc ttcctgccta    1800
actcagtgtt tccacgatgt agcgagcgga atctgcagga gtctgtcctg agtgagcagg    1860
atctgatgca gccagaggaa cccgactacc tgctggatga gatgaccaag gaggccgaaa    1920
tcgacaactc tagtacagtg gagtccctgg gcgagactac cgatatcctg aatatgacac    1980
acattatgtc actgaacagc aatgagaaga gtctgaaact gtcaccagtg cagaagcaga    2040
agaaacagca gactattggc gagctgactc aggacaccgc cctgacagag aacgacgata    2100
gcgatgagta tgaggaaatg tccgagatga aggaaggcaa agcttgtaag cagcatgtga    2160 gtcagggat cttcatgaca cagccagcca caactattga ggctttttca gacgaggaag    2220
tggagatccc cgaggaaaaa gagggcgcag aagattccaa ggggaatgga attgaggaac    2280
aggaggtgga agccaacgag gaaaatgtga agtccacgg aggcaggaag gagaaaacag    2340
aaatcctgtc tgacgatctg actgacaagg ccgaggtgtc cgaaggcaag gcaaaatctg    2400
tcggagaggc agaagacgga ccagagggac gaggggatgg aacctgcgag gaaggctcaa    2460
gcggggctga gcattggcag gacgaggaac gagagaaggg cgaaaaggat aaaggccgcg    2520
gggagatgga acgacctgga gagggcgaaa aagagctggc agagaaggag gaatggaaga    2580 aagggacgg cgaggaacag gagcagaaag aaagggagca gggccaccag aaggagcgca    2640
accaggagat ggaagagggc ggcgaggaag agcatggcga gggagaagag gaagagggcg    2700
atagagaaga ggaagaggaa aaagaaggcg aagggaagga ggaaggagag ggcgaggaag    2760
tggaaggcga gagggaaaag gaggaaggag aacggaagaa agaggaaaga gccggcaaag    2820
aggaaaaggg cgaggaagag ggcgatcagg gcgaaggcga ggaggaagag accgagggcc    2880
gcggggaaga gaaagaggag ggaggagagg tggagggcgg agaggtcgaa gagggaaagg    2940
gcgagcgcga agaggaagag gaagagggcg agggcgagga agaagagggc gaggggaag    3000 aagaggaggg agagggcgaa gaggaagagg gggaggaaa gggcgaagag gaaggagagg    3060 aagggagg agaggaagag ggggaggagg gcgaggggga aggcgaggag gaagaaggag    3120 aggggaagg cgaagaggaa ggcgagggg aaggagagga ggaagaaggg gaaggcgaag    3180
gcgaagagga gggagaagga gaggggagg aagaggaagg agaagggaag ggcgaggagg    3240
aaggcgaaga gggagagggg gaaggcgagg aagaggaagg cgagggcgaa ggagaggacg    3300
gcgagggcga gggagaagag gaggaagggg aatgggaagg cgaagaagag gaaggcgaag    3360
gcgaaggcga agaagagggc gaaggggagg gcgaggaggg cgaaggcgaa ggggaggaag    3420
aggaaggcga aggagaaggc gaggaagaag agggagagga ggaaggcgag gaggaaggag    3480
aggggaggag ggagggagaa ggcgaggggcg aagaagaaga agagggagaa gtggagggcg    3540
aagtcgaggg ggaggaggga gaaggggaag gggaggaaga agagggcgaa gaagaaggcg    3600
```

```
aggaaagaga aaaagaggga gaaggcgagg aaaaccggag aaataggga gaggaggaag    3660 aggaagaggg aaagtaccag gagacaggcg aagaggaaaa cgagcggcag gatggcgagg    3720
aatataagaa agtgagcaag atcaaaggat ccgtcaagta cggcaagcac aaaacctatc    3780
agaagaaaag cgtgaccaac acacagggga atggaaaaga gcagcgaagt aaaatgcctg    3840
tgcagtcaaa acggctgctg aagaatggcc caagcgggtc taaaaaattc tggaacaatg    3900
tcctgccaca ctatctggaa ctgaagtaag cggccgcgcg gatccagaca tgataagata    3960
cattgatgag tttggacaaa ccacaactag aatgcagtga aaaaaatgct ttatttgtga    4020
aatttgtgat gctattgctt tatttgtaac cattataagc tgcaataaac aagttaacaa    4080
caacaattgc attcatttta tgtttcaggt tcagggggag gtgtgggagg tttttagca    4140 tg                                                                  4142
```